(12) United States Patent
Honda et al.

(10) Patent No.: US 9,109,194 B2
(45) Date of Patent: Aug. 18, 2015

(54) DEVICE FOR HARVESTING BACTERIAL COLONY AND METHOD THEREFOR

(75) Inventors: Toshifumi Honda, Yokohama (JP); Hiroko Fujita, Takahagi (JP); Muneo Maeshima, Mito (JP); Akira Maekawa, Hitachinaka (JP); Yoshiko Ishida, Tokyo (JP); Yuta Urano, Yokohama (JP); Shinya Murakami, Fujisawa (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 373 days.

(21) Appl. No.: 13/505,803

(22) PCT Filed: Nov. 5, 2010

(86) PCT No.: PCT/JP2010/069720
§ 371 (c)(1),
(2), (4) Date: Jul. 13, 2012

(87) PCT Pub. No.: WO2011/055791
PCT Pub. Date: May 12, 2011

(65) Prior Publication Data
US 2012/0275681 A1 Nov. 1, 2012

(30) Foreign Application Priority Data

Nov. 5, 2009 (JP) ................................ 2009-253578
Nov. 13, 2009 (JP) ................................ 2009-259649
Nov. 13, 2009 (JP) ................................ 2009-259974
Apr. 7, 2010 (JP) ................................ 2010-088254

(51) Int. Cl.
*G06K 9/00* (2006.01)
*C12M 1/26* (2006.01)

(52) U.S. Cl.
CPC ................................ *C12M 33/00* (2013.01)

(58) Field of Classification Search
USPC ........................................................ 435/304.3
See application file for complete search history.

(56) References Cited

U.S. PATENT DOCUMENTS

| 4,613,573 A | 9/1986 | Shibayama et al. |
| 5,356,793 A | 10/1994 | Koezuka et al. |

(Continued)

FOREIGN PATENT DOCUMENTS

| EP | 0 635 126 B1 | 7/1999 |
| JP | 58-201976 | 11/1983 |

(Continued)

OTHER PUBLICATIONS

Yasue Kon, "Tsurikin no Point", Kensa to Gijutsu, 2007, vol. 35, No. 9, pp. 888-889.

(Continued)

*Primary Examiner* — Amara Abdi
(74) *Attorney, Agent, or Firm* — Baker Botts L.L.P.

(57) ABSTRACT

When multiple kinds of bacterial colonies are present in a petri dish and, for example, a drug tolerance is to be measured, harvesting of mixed colonies of different types of bacteria makes it impossible to accurately determine the drug tolerance. Also, it is required to improve the throughput of a device for harvesting a bacterial colony. From images illuminated from multiple directions, isolating bacterial colonies are automatically extracted. Next, the image feature amounts are calculated from the multiple images that are illuminated from multiple directions and colonies are grouped depending on the feature amounts. Then, bacterial colonies to be harvested are determined based on the results of the grouping.

4 Claims, 25 Drawing Sheets

(56) References Cited

U.S. PATENT DOCUMENTS

| | | | | |
|---|---|---|---|---|
| 7,822,252 B2 * | 10/2010 | Bi et al. | ............ | 382/130 |
| 2007/0070498 A1 | 3/2007 | Endo et al. | | |
| 2007/0206184 A1 * | 9/2007 | Uto et al. | ............ | 356/237.2 |
| 2008/0040044 A1 * | 2/2008 | Dunlay et al. | ............ | 702/19 |
| 2008/0064089 A1 * | 3/2008 | Green et al. | ............ | 435/305.1 |

FOREIGN PATENT DOCUMENTS

| | | | | |
|---|---|---|---|---|
| JP | 59-11173 | | 1/1984 | |
| JP | 62-25348 | | 2/1987 | |
| JP | 62-65700 | | 3/1987 | |
| JP | 63-32477 | | 2/1988 | |
| JP | 3-285696 | | 12/1992 | |
| JP | 7-306023 | | 11/1995 | |
| JP | 8-511676 | | 12/1996 | |
| JP | 9-47281 | | 2/1997 | |
| JP | 10-115612 | | 5/1998 | |
| JP | 2000-6011 | | 1/2000 | |
| JP | 2000-78999 | | 3/2000 | |
| JP | 2000-171360 | * | 6/2000 | ............ G01N 1/10 |
| JP | 2002-98704 | | 4/2002 | |
| JP | 2005-55180 | | 3/2005 | |
| JP | 2005-143425 | * | 6/2005 | ............ C12M 1/34 |
| JP | 2007-54483 | | 3/2007 | |
| JP | 2007-102190 | | 4/2007 | |
| JP | 2008-301737 | * | 12/2008 | ............ C12M 1/34 |

OTHER PUBLICATIONS

Yasue Kon, Tsurikin no Point, Kensa to Gijutsu, 2007, vol. 35, No. 9, pp. 888 and 889 with a partial English translation.

Communication from the Japan Patent Office mailed Feb. 25, 2014, in corresponding Japanese patent application No. 2010-088254.

1977/808458 A, Filing date: Jun. 21, 1977, Robert L. Nelson.

Yasue Kon, "Tsurikin no. Point", Kensa to Gijutsu, 2007, vol. 35, No. 9, Pp. 888-889.

Yasue Kon, "Point of Extracting Bacteria", Journal of Examination and Technology, vol. 35, No. 9. pp. 888-889 Sep. 2007.

* cited by examiner

| ILLUMINATION CONDITION | SHAPE OF BACTERIA COLONY | | |
|---|---|---|---|
| | LOW | HIGH | COMBINED |
| HIGH-ANGLE ILLUMINATION | | | |
| LOW-ANGLE ILLUMINATION | | | |
| TRANSMISSIVE ILLUMINATION | | | |

FIG. 8A
(a)
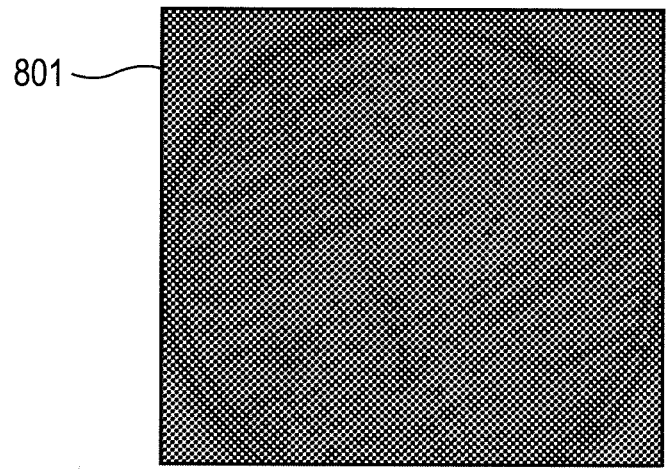
801
(b)
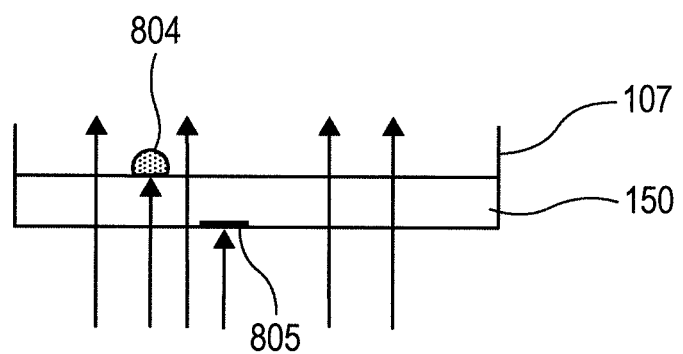
804
107
150
805

FIG. 8B
(a)
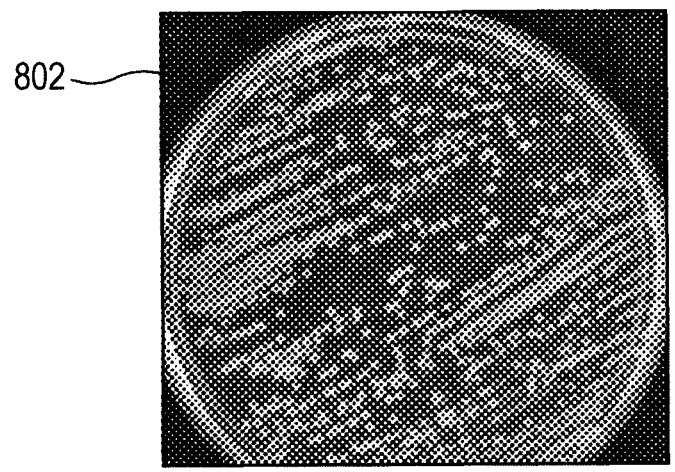
(b)
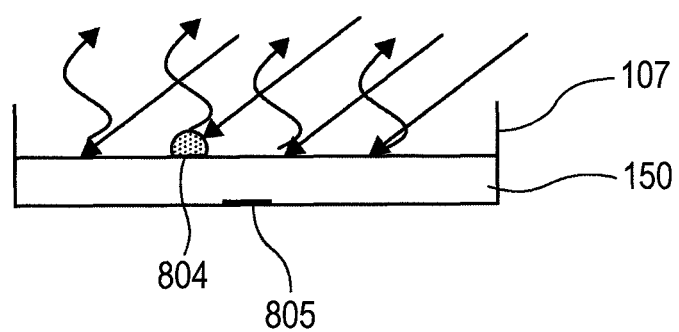

FIG. 8C
(a)
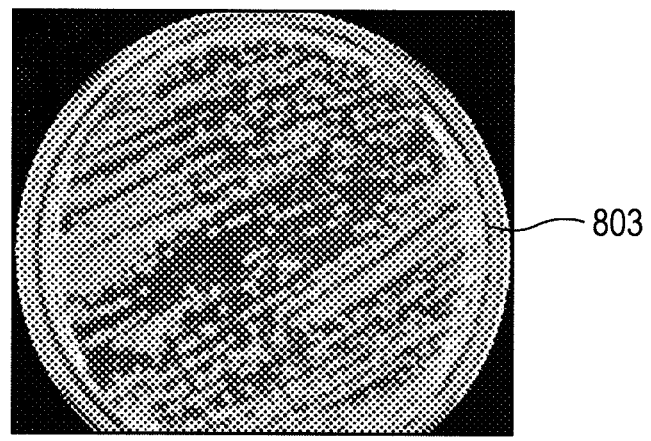
(b)
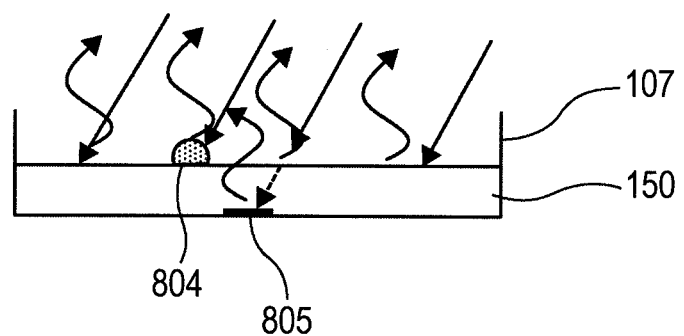

FIG. 12
(a)
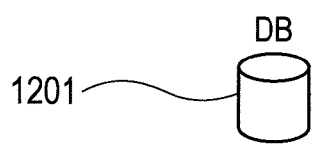
(b)
| BACTERIAL SPECIMEN | MEDIUM | SAMPLE | CULTURE CONDITION | FEATURE AMOUNT DATA |
|---|---|---|---|---|
| 12021 | 12022 | 12023 | 12024 | 12025 |
|  |  |  |  |  |
|  |  |  |  |  |
1202
(c)
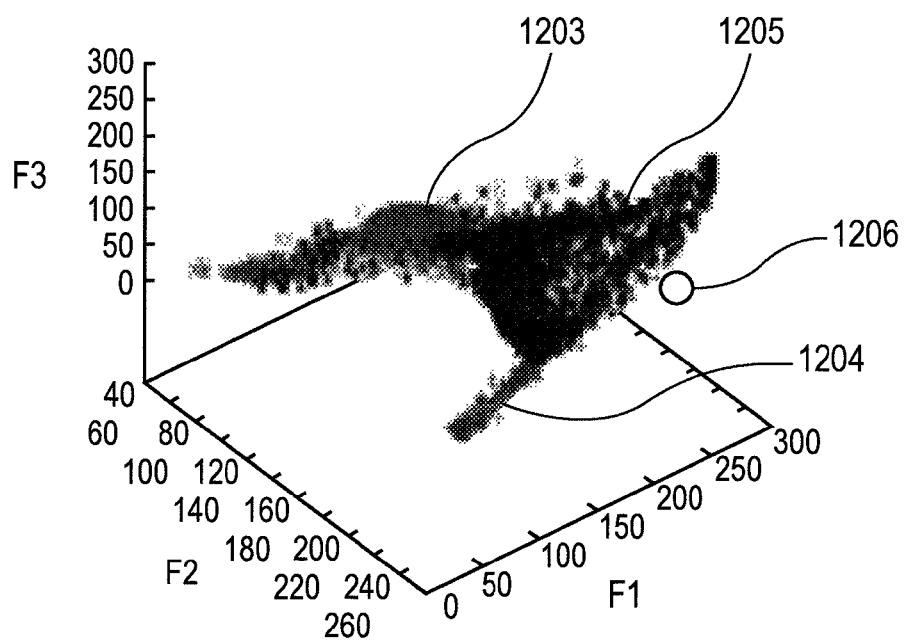

FIG. 26

| COLONY DIAMETER (mm) | NUMBER OF COLONIES REQUIRED TO ACQUIRE PREDETERMINED CONCENTRATION (0.6McF, 3mL) | | | |
|---|---|---|---|---|
| | STAPHYLOCOCCUS EPIDERMIDIS (AFTER 24-HOUR CULTURING) | STAPHYLOCOCCUS EPIDERMIDIS (AFTER 48-HOUR CULTURING) | STAPHYLOCOCCUS AUREUS (AFTER 24-HOUR CULTURING) | PSEUDOMONAS AERUGINOSA (AFTER 24-HOUR CULTURING) | ESCHERICHIA COLI (AFTER 24-HOUR CULTURING) |
| 0.5 | 56<br>40 | (McF 0.41 AT 44 CFU) | 150 | 50<br>45<br>48 | 300 TO 600 |
| 1.0 | 13<br>11<br>11 | 9<br>9<br>8 | 15<br>18<br>27 | | 13 TO 14 |
| 1.5 | NOT GROWN | 3<br>3<br>3 | 5<br>5<br>6 | NOT GROWN | 5 TO 6 |
| 2.0 | | 2 | 3<br>3<br>3 | | 2 TO 3 |

DEVICE FOR HARVESTING BACTERIAL COLONY AND METHOD THEREFOR

TECHNICAL FIELD

The present invention relates to a device for harvesting a bacterial colony cultured in a petri dish, and particularly, to a device for harvesting a bacterial colony and a method thereof that image an optical image of a petri dish, automatically classify a plurality of kinds of bacterial colonies cultured in the petri dish based on the imaged image for each same bacterial species, harvest a plurality of bacterial colonies for each bacterial species, and identify harvested bacteria.

Further, the present invention relates to a device for harvesting a bacterial colony and a method thereof, and particularly, to a preprocessing apparatus that cultures bacteria in a specimen, selects a bacteria colony, and adjusts a bacterial liquid of the selected bacterial colony in order to perform identification and drug susceptibility test of bacteria included in the specimen.

In addition, the present invention relates to a device for harvesting a bacterial colony and a method thereof, and particularly, a preprocessing apparatus for harvesting a bacterial colony for an apparatus and a method for analyzing bacteria that test identified drug susceptibility.

BACKGROUND ART

In testing bacteria with respect to a specimen, a method of culturing the bacteria in a culture medium within a petri dish and harvesting the bacteria has been used. In this method, in general, a suspension of the bacteria is smeared to the culture medium and the bacteria are cultured in a constant-temperature bath and thereafter, optically visually observed, and a target bacterial colony is harvested. The harvested bacteria are used for the purpose of testing antibiotic tolerance. A method of testing the antibiotic tolerance of the bacteria is disclosed in detail in Patent Literature 1. In a minimum inhibitory concentration (MIC) method, a diluted liquid of an antibiotic substance is injected into a liquid medium or a solid medium, the harvested bacteria colony the medium with the harvested bacterial colony, and a growing condition of the bacteria is observed by culturing the bacteria. A culturing condition is observed in a plurality of media by variously changing the concentration of the diluted liquid of the antibiotic substance, thereby making it possible to acquire a minimum antibiotic substance concentration which cannot be grown and an appropriate drug concentration capable of reducing a burden to a patient can be determined.

Meanwhile, Patent Literature 2 discloses a bacterial colony transferring apparatus in which a bacterial colony within a petri dish is photographed with a television camera, a tester visually verifies an image projected on a monitor and indicates a bacterial colony to be harvested to automatically move a pick-up to the position of the bacterial colony, harvests the bacterial colony, and transfers the harvested bacterial colony to a test tube.

Further, Patent Literature 3 discloses a method of analyzing a result of harvesting using filtering after liquefying a specimen with a Fourier transform infrared spectrophotometer (FT-IR) or a microscopic infrared spectrophotometer and comparing a waveform of spectral absorbance with a waveform registered in a database to identify the waveform.

A microbial analysis apparatus is used to, in testing a specimen in a medical practice, identify a species of a microorganism included in the specimen and measure susceptibility of the microorganism to an antibiotic. Establishing a therapeutic measure by determining a kind and a concentration of a drug which is effective with respect to the microorganism detected from the specimen is very important to perform appropriate antimicrobial therapy.

Herein, one example of a flow of testing a specimen will be described below. First, collected specimens (for example, blood, sputum, feces, and the like) are dyed and observed with a microscope. When a positive reaction is observed, the specimens are moved onto a medium (for example, agar, and the like) of a petri dish and the petri dish is inputted into an incubator. One day after, when the petri dish is extracted from the incubator, a plurality of kinds of bacterial colonies of microorganisms are generated on the medium. One kind of microorganism is selected and harvested among the plurality of kinds of bacterial colonies and moved to the test tube and bacterial liquids having a plurality of kinds of concentrations are adjusted by adjusting the concentration thereof with normal saline. The bacterial liquids adjusted to the plurality of kinds of concentrations are inputted into a microorganism testing apparatus, and identification of bacteria and drug susceptibility are examined.

In order to rapidly and accurately test the specimen, a microorganism analysis apparatus that automates each work is proposed. For example, Patent Literature 4 discloses an automatic analysis apparatus of bacteria. The automatic analysis apparatus of bacteria disclosed in Patent Literature 1 includes a test liquid preparing unit, a pre-incubation, a top agar dispensing unit, a plating unit, a plate receiving unit, a bacterial colony counting unit, a data processing unit, a test tube transferring means, and a plate receiving rack transferring means and can automatically perform a series of analysis operations of counting the number of bacterial colonies with high precision in preparing the test liquid.

Patent Literature 5 discloses a microorganism screening apparatus including an image processing apparatus detecting a position of a bacterial colony, an elevator unit transferring a work with a rotating operation mechanism and an ascending and descending operation mechanism, a harvesting/inoculating unit that performs harvesting and inoculating while determining harvesting and inoculating positions by operating a robot, a work transporting unit moving and transporting the work, a cover opening/closing unit controlling opening/closing a cover of the work, a liquid dispensing unit performing dispensing of a liquid medium, an agar dispensing unit dispensing an agar medium, and a host computer unit performing control operations such as management of data of microorganism resources, a command of an operation mode, and the like. The microorganism screening apparatus disclosed in Patent Literature 5 aims at automating various operations required for screening a soil microorganism and further, improving reliability by completely managing a strain and data.

Patent Literature 6 discloses a method and an apparatus for testing a microorganism colony. The method and apparatus for testing the microorganism colony disclosed in Patent Literature 6 may compare an image of a petri dish, an image before a bacterial colony is generated, and an image after the bacterial colony is generated, remove contamination of a photographing system or a residue on a medium from the image after the bacterial colony is generated, and accurately count the number of bacterial colonies. It is described that, by combining a mark printed on the petri dish with each image in advance, the images may be accurately compared with each other.

Patent Literature 7 discloses a method and an apparatus for collecting a bacteria colony. The method and apparatus for collecting a bacteria colony disclosed in Patent Literature 7 aims at installing a position reference means of a bacterial colony, determining an absolute spatial position of the bacterial colony, and accurately determining a place of a harvested bacterial colony.

In infectious disease therapy, establishing a therapy measure by identifying mastoiditis, rapidly measures susceptibility to antibiotic, and determining an effective drug is important for appropriate antimicrobial therapy. In general, a presented specimen is applied to a medium and cultured, bacterial suspension is prepared by harvesting the generated bacterial colony and suspending the harvested bacterial colony to normal saline, and the bacterial suspension is inoculated into a measuring device of an identification and drug susceptibility testing apparatus. In identification and susceptibility testing, it is required to make the amount of bacteria inoculated into the device constant at predetermined concentration with accuracy and high reproducibility, in order to acquire an accurate result. In most cases, in order to acquire a predetermined amount of bacteria, a plurality of same kinds of bacterial colonies are selected and harvested among bacterial colonies grown on a petri dish, suspended to a liquid such as normal saline within one vessel, and prepared with a predetermined concentration (the number of bacteria) by measuring turbidity or opacity. Kinds of mixed bacterial colonies should be the same as each other and a plurality of kinds of bacterial colonies are generally grown on the same petri dish, and a high-level technique is required of a laboratory technician in selecting the same kind of bacterial colonies among them. Further, since the same kind of bacterial colonies are selected from various large and small-sized bacterial colonies, it is required that turbidity is first adjusted and thereafter, the bacterial colonies are added or normal saline for dilution is added in order to acquire predetermined turbidity, and as a result, it is complicated and it takes some time. Therefore, the method and apparatus for collecting a bacteria colony are not appropriate to mass processing. As a related art to make the amount of harvested bacteria per one time constantly, a simple kit has been commercialized, which can acquire a predetermined concentration of bacterial liquid by harvesting a predetermined amount of bacteria and suspending the harvested bacteria to a predetermined amount of normal saline. For example, a method disclosed in Patent Literature 8 discloses an example capable of collecting a predetermined amount of bacteria by using a simple stick body with a groove. However, in this method, a concentration and the amount of bacterial liquid acquired are limited, and as a result, only a small amount of bacterial liquid with a comparatively low concentration range can be acquired.

Meanwhile, Patent Literature 2 discloses, as a bacterial colony transferring apparatus, a method in which the bacterial colony within a petri dish is photographed with a television camera, the laboratory technician visually verifies an image projected on a monitor and selects and indicates a bacterial colony to be harvested to automatically move a harvesting tool to the position of the bacterial colony according to the indication, harvest the bacterial colony, and transfer the harvested bacterial colony to a test tube. However, in this method, the image which the laboratory technician photographs by using the television camera is verified through the monitor to select the harvested bacterial colony one by one, and as a result, even though the apparatus is used, an effect of rapidity is slight.

Similarly, Patent Literature 9 and Patent Literature 10, as the bacterial colony transferring apparatus, discloses a method in which a laboratory technician verifies an image photographed by a television camera through a monitor, inputs a condition such as the size of a bacterial colony to be selected or indicates a bacterial colony to be excluded, and as a result, a bacterial colony to be harvested is automatically transferred to a new medium. In this method, the bacterial colonies grown on the petri dish are basically all the same bacterial species and all bacterial colonies other than an exception grown by contamination and the like are transferred, and since the apparatus is unmanly operated by inputting only a condition, significant power saving is achieved. However, by harvesting the bacterial colony one by one from the petri dish before transferring and transferring the bacterial colony to a medium of a new petri dish one by one, the bacterial colony need not be mixed, and as a result, a type of the bacterial colony is not discriminated.

In preparing the bacterial liquid for identification testing or drug susceptibility testing intended in the present invention, a plurality of same kind of bacteria needs to be harvested from one petri dish and different kinds of bacteria need to be excluded and only a single kind of bacteria needs to be selected from the image acquired by the television camera. However, since a comprehensive feature of the bacterial colony cannot be normally extracted by only one image acquired by using the television camera, an error may occur when the bacterial colony is selected. Meanwhile, a bacterial colony counter that measures the number of bacterial colonies including bacterial colonies on the agar medium as well as the surface of the petri dish has been available in the market. This processes a 2D image photographed by the camera and measures the number of bacterial colonies having a size larger than a size suitable for the condition and similarly, cannot discriminate different kinds of bacterial colonies. In the above example, the acquired image is based on plane information and the size of the bacterial colony can be measured, but information on a shape or a height direction of the bacterial colony cannot be acquired.

CITATION LIST

Patent Literature

Patent Literature 1: Japanese Patent Application Laid-Open Publication No. 63-32477
Patent Literature 2: Japanese Patent Application Laid-Open Publication No. 59-11173
Patent Literature 3: Japanese Patent Application Laid-Open Publication No. 2005-55180
Patent Literature 4: Japanese Patent Application Laid-Open Publication No. 2002-98704
Patent Literature 5: Japanese Patent Application Laid-Open Publication No. 9-47281
Patent Literature 6: Japanese Patent Application Laid-Open Publication No. 2005-143425
Patent Literature 7: Japanese Patent Application Laid-Open Publication No. 2000-171360
Patent Literature 8: Japanese Patent Application Laid-Open Publication No. 58-201976
Patent Literature 9: Japanese Patent Application Laid-Open Publication No. 62-25348
Patent Literature 10: Japanese Patent Application Laid-Open Publication No. 62-65700
Patent Literature 11: Japanese Patent Application Laid-Open Publication No. 2000-78999
Patent Literature 12: Japanese Patent Application Laid-Open Publication No. 7-306023

SUMMARY OF INVENTION

Technical Problem

In order to implement an MIC method, since bacteria need to be cultured in a plurality of media in which the concentration of the antibiotic substance is changed, a plurality of bacterial colonies cultured in the petri dish need to be harvested. When a relatively small bacterial colony is not also harvested, a long time is required until the bacterial colony is harvested after being cultured in the petri dish and culturing within a short time is difficult.

Further, in the MIC method, when all kinds of harvested bacterial colonies are not the same as each other, accurate tolerance of the antibiotic substance cannot be tested, but up to now, the tolerance depends on the visual result of the tester, such that traceability cannot be acquired. In addition, visual testing may be different according to a technique of the tester, such that only a few testers cannot but test the tolerance to acquire stable harvesting and a plurality of specimens cannot be processed.

Meanwhile, as a bacterial colony transferring apparatus disclosed in Patent Literature 2, in a method in which the bacterial colony within the petri dish is imaged with a television camera, the tester verifies an image projected on a monitor and indicates a bacterial colony to be harvested to automatically move a pick-up to the position of the bacterial colony, harvest the bacterial colony, and transfer the harvested bacterial colony to a test tube, since the tester selects the harvested bacterial colonies one by one by verifying the television camera, a man hour of the tester is not so reduced. Further, in one image acquired by the television camera, an error occurs in selecting the bacterial colony in some cases. For example, an appearance of any kind of bacteria is apparent by transmitted illumination and other bacteria tend to be apparent by illumination from the top. When the MIC method is used, a plurality of same kind of bacteria need to be harvested, and as a result, different kinds of bacteria need to be excluded and only a single kind of bacterium needs to be selected from the image acquired through the television camera and the bacterial colony cannot be discriminated with sufficient precision by only the image of the television camera.

Further, in the method disclosed in Patent Literature 3 in which after the specimen is liquefied, a bacteria collection result by filtering is analyzed by FT-IR and the waveform of spectral absorbance is compared with the waveform registered in a database to identify the waveform, culturing for using the MIC method after analysis through the FT-IR is impossible.

A first object of the present invention is to provide a device for harvesting a bacterial colony and a method thereof that can specify bacterial colonies of the same kind to be harvested among bacterial colonies group and stably harvest the plurality of specified bacterial colonies by solving a known technical problem.

In general, culturing the bacterial colony requires a time over one night, but hundreds or more of petri dishes may be tested according to a scale of a test room. Culturing the bacterial colony in the hundreds of petri dishes one by one, selecting an appropriate bacterial colony from the plurality of bacterial colonies grown in the petri dish and harvesting the appropriate bacterial colony by the harvesting tool, and diluting the petri dish with normal saline or adding the bacterial colony, and adjusting the bacterial suspension while monitoring whether the bacterial colony has desired turbidity require a lot of time and manpower cost. Therefore, development of an apparatus that can automate the work from the growth of the bacterial colony to the adjustment of the bacterial suspension is required.

The analysis apparatus disclosed in Patent Literature 4 does not have the means for selecting the bacterial colony. Further, in Patent Literature 5, Patent Literature 6, and Patent Literature 7, since position detection and harvesting of the bacterial colony are performed with one image, selection and harvesting of the bacterial colony cannot be performed in parallel, such that it is difficult to improve a processing speed.

Therefore, a second object of the present invention is to provide a device for harvesting a bacterial colony and a method thereof that can perform selection and harvesting of the bacterial colony in parallel and improve the processing speed.

Further, an object to be achieved in the present invention is to estimate height-direction information of collected bacterial colonies, automatically calculate the volume of the bacterial colony, and automatically harvest the required number of bacterial colonies with respect to individual bacterial colonies in order to collect a predetermined quantity of bacterial colonies required for an identification and susceptibility test after discriminating the bacterial colonies for each same kind by the image of the petri dish acquired through imaging, and determining and selecting the bacterial colony to be harvested.

Further, a method and an apparatus for automatically preparing a bacterial liquid having predetermined turbidity are provided after automatic harvesting according to acquired information by adopting this method, such that an apparatus and a method for analyzing a microorganism with rapidity and high power saving effect are provided, thereby reducing the manpower cost of a bacteria test room.

Solution to Problem

In order to achieve the objects, in the present invention, a device for harvesting a bacterial colony is configured to include: an upper illumination means illuminating a bacteria colony cultured on a culture medium received in a first vessel which is optically transparent, from the top; a transmitted illumination means illuminating the bacterial colony by transmitting the optically transparent vessel and the culture medium with illumination light; an imaging means imaging the bacterial colony sequentially illuminated by the upper illumination means and the transmitted illumination means; an image processing means extracting an image of a bacterial colony to be harvested by processing an image of the bacterial colony illuminated by the upper illumination means and an image of the bacterial colony illuminated by the transmitted illumination means, which are imaged by the imaging means; and a harvesting means harvesting the bacterial colony extracted by the image processing means from the culture medium and moving the harvested bacterial colony to a second vessel.

Further, a method for harvesting a bacterial colony according to the present invention includes: illuminating a bacteria colony cultured on a culture medium received in a first vessel which is optically transparent, from upper side and imaging the bacterial colony to acquire an upper side illumination image of the bacterial colony; illuminating the bacterial colony by transmitting the optically transparent vessel and the culture medium with illumination light and imaging the bacterial colony to acquire a transmitted light illumination image of the bacterial colony; extracting an image of a bacterial colony to be harvested by processing the upper side illumination image and the transmitted light illumination image; and harvesting a bacterial colony corresponding to the extracted image from the culture medium and moving the harvested bacterial colony to a second vessel.

Further, in order to achieve the object, the present invention provides a device for harvesting a bacterial colony, including: a specimen stage on which a petri dish is loaded; an imaging stage imaging the inside of the petri dish from a top surface of the petri dish and having a storage means storing the image; a selection means automatically detecting bacterial colonies of microorganisms in the petri dish and selecting some of the detected bacterial colonies; an image display means displaying the image in the petri dish from the top surface of the petri dish; a comparison means reading the image imaged with the imaging stage from the storage means and comparing the read image with the image displayed with the image display means; a harvesting means including a driving unit for harvesting the bacterial colonies of the microorganisms in the petri dish; a harvesting stage including the harvesting means, the image display means, the comparison means, and the selection means; a first buffer station storing a plurality of petri dishes before imaging; a second buffer station storing a plurality of petri dishes after imaging; a first transportation means sequentially supplying petri dishes before imaging from the first buffer station to the imaging stage; a second transportation means sequentially supplying petri dishes after imaging from the imaging stage to the second buffer station; a third transportation means sequentially supplying petri dishes before harvesting from the second buffer station to the harvesting stage; and a control unit controlling the imaging stage, the harvesting stage, the first buffer station, the second buffer station, the first transportation means, the second transportation means, and the third transportation means, wherein the selection means automatically selects a bacterial body to be harvested from an appearance feature of the bacterial colony in the imaged petri dish with respect to each petri dish.

Further, in order to achieve the object, the present invention provides a device for harvesting a bacterial colony, including: a specimen stage on which a petri dish is loaded; an imaging stage imaging the inside of the petri dish from a top surface of the petri dish and having a storage means storing the image; a selection means automatically detecting bacterial colonies of microorganisms in the petri dish and selecting some of the detected bacterial colonies; an image display means displaying the image in the petri dish from the top surface of the petri dish; a comparison means reading the image imaged with the imaging stage from the storage means and comparing the read image with the image displayed with the image display means; a harvesting means including a driving unit for harvesting the bacterial colonies of the microorganisms in the petri dish; a harvesting stage including the harvesting means, the image display means, the comparison means, and the selection means; a first buffer station storing a plurality of petri dishes before imaging; a second buffer station storing a plurality of petri dishes after imaging; a first transportation means sequentially supplying petri dishes before imaging from the first buffer station to the imaging stage; a second transportation means sequentially supplying petri dishes after imaging from the imaging stage to the second buffer station; a control unit controlling the imaging stage, the harvesting stage, the first buffer station, the second buffer station, the first transportation means, and the second transportation means, wherein the imaging stage and the harvesting stage are positioned within a common area.

The present invention includes a camera, a base on which the bacterial camera on the culture medium to be imaged is mounted, a plurality of first illumination units radiating light to the bacterial colony from different positions on the top, and a second illumination units illuminating the culture medium from the bottom, which is positioned at an opposite side to the camera with respect to the base.

Advantageous Effects of Invention

According to the present invention, by using the image acquired by illuminating the petri dish from the top and the image acquired by transmitting and illuminating the petri dish from the bottom, the image of the bacterial colony may be separated from an image of a character or a symbol written or formed on the petri dish to be detected and the bacterial colony species may be classified and accurately harvested by image processing.

Further, illumination from upper side is performed in a plurality of elevation angle/direction angle directions and an illumination image from multiple directions is used to make almost every bacterial colony on the medium apparent, the accurate position of the bacterial colony is feasible, and an appearance feature of the bacterial colony is calculated from the illumination image from the multiple directions, thereby achieving accurate grouping. In addition, a plurality of images illuminated and imaged from different directions are displayed on the screen, such that it is easy for even a user to visually verify different kinds of bacteria.

Further, according to the present invention, selection and harvesting of the bacterial colony can be performed in parallel and the throughput in testing the microorganism can be improved.

In addition, according to the present invention, since the height information of the bacterial colony is estimated and the volume of the bacterial colony is calculated from a plurality of first illumination units radiating light to the bacterial colony from different positions from upper side and a second illumination unit illuminating the medium from the bottom, which is positioned at an opposite side to the camera with respect to a base, a quantity required to acquire a bacterial liquid having predetermined concentration (turbidity) can be estimated. As a result, accuracy of the quantity of collected bacterial colonies can be improved, the work such as addition or dilution of the bacterial colony can be remarkably reduced, and the bacterial liquid having the predetermined concentration can be rapidly prepared.

Consequently, a time required for the entire bacterial test can be shortened.

BRIEF DESCRIPTION OF DRAWINGS

FIG. 8A is a cross-sectional view of a petri dish showing (a) an imaged image by transmitted illumination and (b) a transmitted illumination direction in the first embodiment.

FIG. 8B is a cross-sectional view of the petri dish showing (a) an imaged image by low-angle illumination and (b) a low-angle illumination direction in the first embodiment.

FIG. 8C is a cross-sectional view of the petri dish showing (a) an imaged image by high-angle illumination and (b) a high-angle illumination direction in the first embodiment.

FIGS. 12(a), 12(b), and 12(c) are a database describing a classification method of the bacterial colony of the bacteria in the first embodiment, a table showing one example of an index of the database, and a graph showing the distribution of feature vectors, respectively.

FIG. 26 is an example of the quantity of harvested bacteria required to acquire predetermined turbidity.

DESCRIPTION OF EMBODIMENTS

Hereinafter, embodiments of the present invention will be described with reference to the accompanying drawings.

First Embodiment

Figure 1:
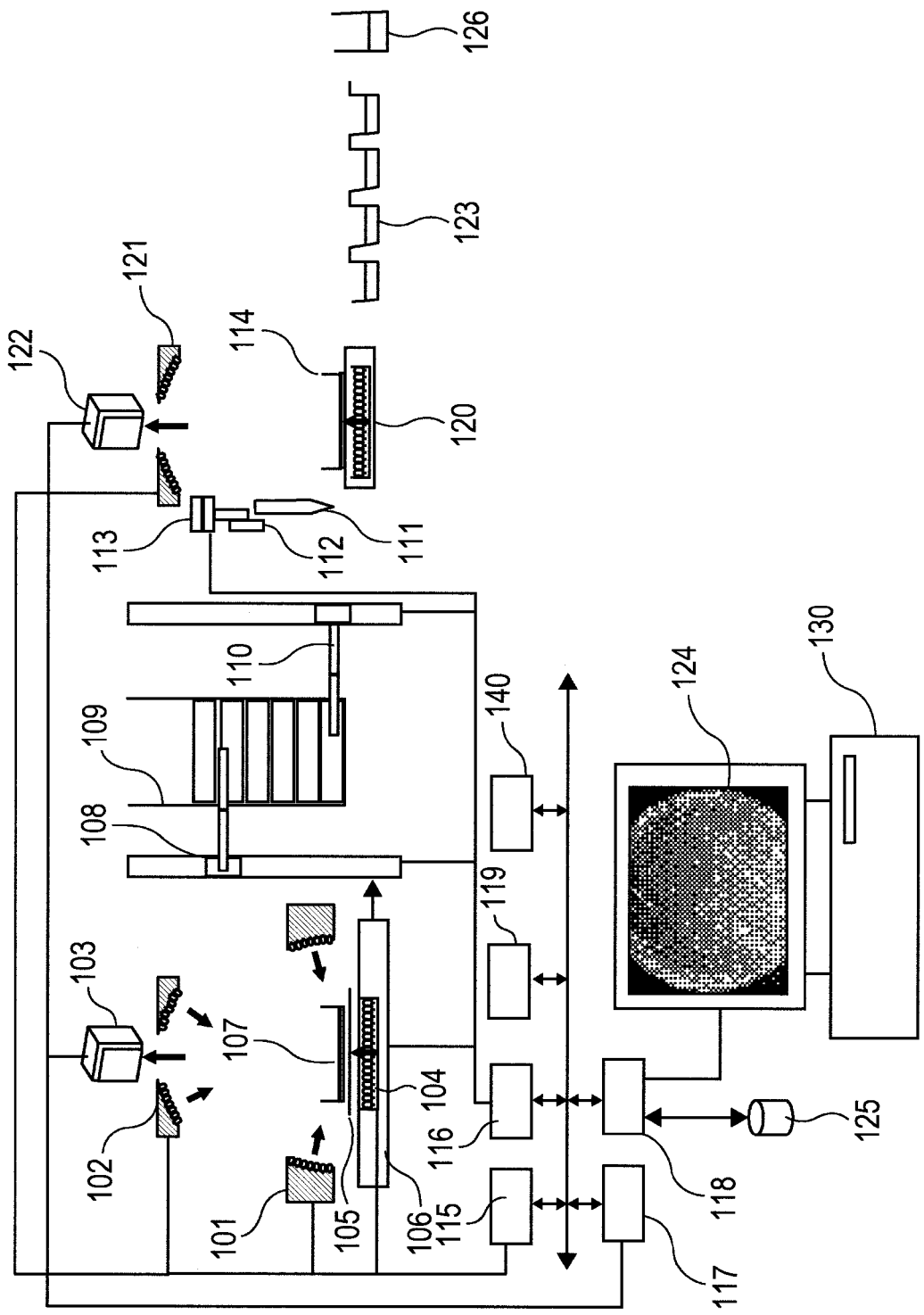
FIG. 1 is a block diagram showing a schematic configuration of an entire system according to a first embodiment.

An overall configuration of an automatic harvesting device 100 will be shown in FIG. 1. Reference numeral 101 represents a low-angle illumination unit, reference numeral 102 represents a high-angle illumination unit, reference numeral 103 represents a camera, and reference numeral 104 represents a transmitted illumination unit. It is preferable that the camera of reference numeral 103 is capable of acquiring color information. Reference numeral 105 represents a light shielding plate, reference numeral 106 represents a base, and reference numeral 107 represents a petri dish. A medium 150 of bacteria is provided within the petri dish of reference numeral 107 and a bacterial colony acquired from a specimen to be subjected to a test is cultured thereon. As the bacterial colony, for example, a bacterial colony is used, which is cultured within a constant-temperature bath for approximately 24 H. Reference numerals 101, 102, and 104 are connected to a light control unit 115, light-on and light-off of reference numerals 101, 102, and 104 may be controlled, and reference numerals 101, 102, and 104 may be lit on through a predetermined combination thereof.

As the light shielding plate 105, for example, a movable diaphragm or a liquid crystal shutter is used. The surface of the movable diaphragm is subjected to opaque black painting and liquid crystals are subjected to anti-reflection treatment. When the transmitted illumination unit 104 is lit on, illumination light is set to illuminate the petri dish 107 and further, when the low-angle illumination unit 101 and the high-angle illumination unit 102 are lit on, a bottom surface of the petri dish 107 is darkened. In general, characters may be printed on the bottom surface of the petri dish 107. This has an effect to prevent the characters from being apparent when the illumination of the low-angle illumination unit 101 or the high-angle illumination unit 102 is turned on.

Reference numeral 103 represents imaging means and an imaged image is transmitted to an image input means 117. Reference numeral 119 represents image processing means, and extracts an area of the bacterial colony by processing image data transmitted to the image input means 117 and further, calculates an image feature amount from each extracted bacterial colony by using image processing. The image feature amount includes, for example, a boundary length, an area, color information, luminosity information, and a difference from background luminosity of the bacterial colony area. Reference numeral 118 represents grouping means and inputs the image inputted by using the image input means 117, a bacterial colony area 119, and the image feature amount. Reference numeral 125 represents a secondary storage device and may store the imaged image, the processed image, data, and the position and the area of the bacterial colony. Further, reference numeral 125 may conserve the image feature amount.

The grouping means 118 performs grouping based on distribution of feature amounts stored every correspondence between the medium 150 that has already acquired and a group of bacteria having a similar appearance, which is stored in the secondary storage device 125. A bacterial colony to be harvested or a candidate thereof is automatically determined based on the group acquired herein. The grouping result is displayed on a GUI 124 of an input/output terminal 130 and a tester may verify the grouping result and the candidate to be harvested.

When the grouping result is different from an intention of the tester, the tester registers different grouping in the grouping means 118 through the GUI 124. For example, several bacterial colonies to be harvested are designated from the image, an image feature amount of a bacterial colony close to the designated bacterial colonies is analyzed, and bacterial colonies having an image feature amount similar to the image feature amount are grouped as a bacterial colony species to be harvested. The grouping means 118 extracts the candidate of the bacterial colony to be harvested and displays the extracted candidate to the tester on the GUI 124, based on a rule which the tester designates through the GUI from the grouping result.

The grouping rule includes, for example, the following:
1) A group closest to the center of the feature amount among the groups,
2) A group having the size close to a predetermined size, and
3) A group close to a feature amount of a bacterial colony designated by the tester.

In addition to the verification mode using the GUI, an automatic operation mode is also provided and in the case of the automatic operation mode, a bacterial colony selected by a system is just harvested without the tester's verification.

Reference numeral 108 represents transportation means of the petri dish and is used for the purpose of storing the imaged petri dish 107 in a stacker 109. The petri dish may be transported by the petri dish transportation means 108 after grouping using the grouping means 118 or the image processing using the image processing means 119 or before the image processing or the grouping. When a verification operation of the grouping result by the tester is required, a comparatively long time is frequently required for the operation. Therefore, in order to increase throughput of the device, when imaging of the image is completed, an image of a subsequent petri dish 107 is inputted without waiting for the tester's verification operation and the tester preferably verifies and modifies the grouping result and determine the bacterial colony to be harvested by using the image which has been already acquired. Reference numeral 110 also represents the transportation means of the petri dish and is used for the purpose of transporting the petri dish from the stacker to a harvesting area.

Reference numeral 111 represents a harvesting needle, reference numeral 112 represents a Z stage, and reference numeral 113 is an XY stage and the petri dish transportation means 108 and 110, the Z stage 112, and the XY stage 113 are controlled by a stage control unit 116. A petri dish 114 transported from the stacker is illuminated by a transmitted illumination unit 120 and an upper illumination unit 121, the image may be imaged by using a camera 122, and the imaged image may be inputted by using the image input means 117.

The image inputted into the image input means 117 is compared with the image acquired by using the camera 103 in the image processing means 119 and a position deviation when the same petri dish is transported through the stacker is corrected. For example, the image imaged by using the camera 103 is represented by I0 and the image imaged by the camera 122 is represented by I1. The image I0 and the image I1 are imaged so that illumination conditions most coincide with each other in two optical systems. By setting a background of the petri dish 107 to be black, the petri dish 107 is imaged brightly, and as a result, a petri dish area may be extracted by binarization processing. The petri dish area is acquired by each of the image I0 and the image I1 and substantially matched with a rotational center of the petri dish 107. In order to prevent an influence of a flash of the petri dish 107, luminosities at an edge of the petri dish 107 and at the outside thereof are set to be black in terms of image processing. Thereafter, a spectrum image F(I0) by using 2D Fourier transform of the image I0 and 2D Fourier transform F(I1) of the image I1 are acquired. Since the Fourier-transform spectrum image is not changed with respect to the position deviation of the image, a difference between two images is only a rotation-direction deviation of the petri dish.

In order to reduce an influence of an unevenness of brightness caused by a difference between the imaged images of the camera 103 and the camera 122, when log transform is performed with respect to each of F(I0) and F(I1) and thereafter, a DC element of Fourier transform is set as an original point, a distance from the original point is set as r and a rotational element around the original point is set as θ, and local image transform of r-θ is performed. The images are set as an image I2 and an image I3. The images of the image I2 and the image I3 are Fourier-transformed only in a θ direction of local coordinate transform. A product of the Fourier-transformed images is acquired by a correlation theorem and inversely Fourier-transformed to acquire inter-correlation coefficients of respective r positions. By adding up the respective inter-correlation coefficients, a 1D inter-correlation coefficient for θ of the entire image is acquired and a peak thereof is calculated as a rotational deviation amount.

Subsequently, the I0 image is rotation-transformed as large as an angle of the rotational deviation and an XY-direction deviation amount of the I0 image and the I1 image is calculated by normalized inter-correlation. A center coordinate in rotation-transforming is (cx, cy). Further, a deviation amount is (Δx, Δy, θ0). When the position of the bacterial colony imaged by the camera of reference numeral 103 is (x, y), the position (x', y') of the bacterial colony in the image of reference numeral 122 is represented by the following equation.

$$x' = (x-cx)\cos\Delta\theta - (y-cy)\sin\Delta\theta + \Delta x$$

$$y' = (x-cx)\sin\Delta\theta + (y-cy)\cos\Delta\theta + \Delta y \quad \text{(Eq. 1)}$$

Further, the coordinate matching method using the 2D Fourier transform is one embodiment and besides, other methods including a method using normalized correlation calculation may be adopted.

Reference numeral 123 represents a micro plate and a plurality of wells are placed. In the respective wells, for example, Ca ions of 50 mg/l, Ca ions of 25 mg/l, and a drug for evaluating tolerance to bacteria are added to a Muller Hinton culture liquid so as to have different concentrations in the respective wells. Other liquid media may be used and further, solid media may be used. By controlling the Z stage 112 and the XY stage 113, the harvesting needle 111 is moved to a coordinate of the bacteria to be harvested of the petri dish 114 to pick up the bacterial colony. In order to pick up the bacterial colony, a force sensor (not shown) is preferably mounted at a mounting position of the harvesting needle 111 to allow a point where the harvesting needle 111 contacts the solid medium to be sensed. Thereafter, the bacterial colony is put into a vessel 126 into which normal saline or a liquid medium is put. This operation is performed with respect to several bacterial colonies and after the concentration of the bacterial colony in the vessel 126 becomes sufficient, a suspension in the vessel 126 is put into any one well on the micro plate 123.

The harvesting needle 111 is changed to another one every time different bacterial colony species are harvested up. There is a case in which a sufficient number of bacterial colonies cannot be cultured within one petri dish. In this case, there is a case in which bacteria cannot be cultured in all of set wells on the micro plate 123, in one petri dish. Therefore, in this case, bacteria of the specimen are cultured in the plurality of petri dishes, a particular bacteria species is determined from the plurality of petri dishes, and the particular bacteria in the plurality of petri dishes are moved to one micro plate 123 from the plurality of petri dishes. As a result, the MIC method may be executed even at a comparatively short culture time. As described above, when the bacterial colony to be harvested is selected from the plurality of petri dish images, the plurality of petri dish images of the same specimen need to be easily displayed in the GUI 124 of the input/output means 130. The entirety of the automatic harvesting device 100 is controlled by an entire control unit 140.

FIG. 2 shows a detailed configuration of illumination means such as the low-angle illumination unit 101 and the high-angle illumination unit 102. The low-angle illumination unit 101 is constituted by division light sources 2011, 2012, 2013, and 2014 and light-on thereof may be individually controlled by using the light control unit 115. The high-angle illumination unit 102 is constituted by division light sources 2021, 2022, 2023, and 2024 and light-on thereof may also be individually controlled by using the light control unit 115. Since the surface of the bacterial colony is comparatively smooth, a directly reflected place is imaged brightly by the illumination of the surface.

Figure 2A:
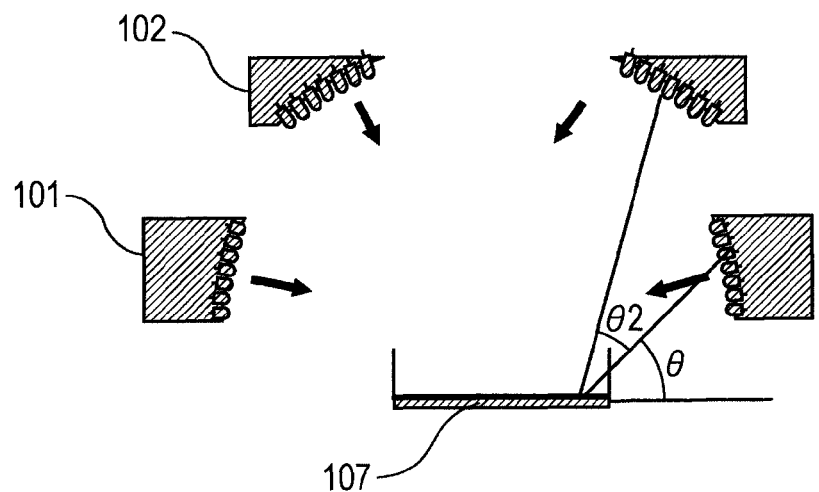
FIG. 2A is a front view showing a schematic configuration of an illumination system according to the first embodiment.
Figure 2B:
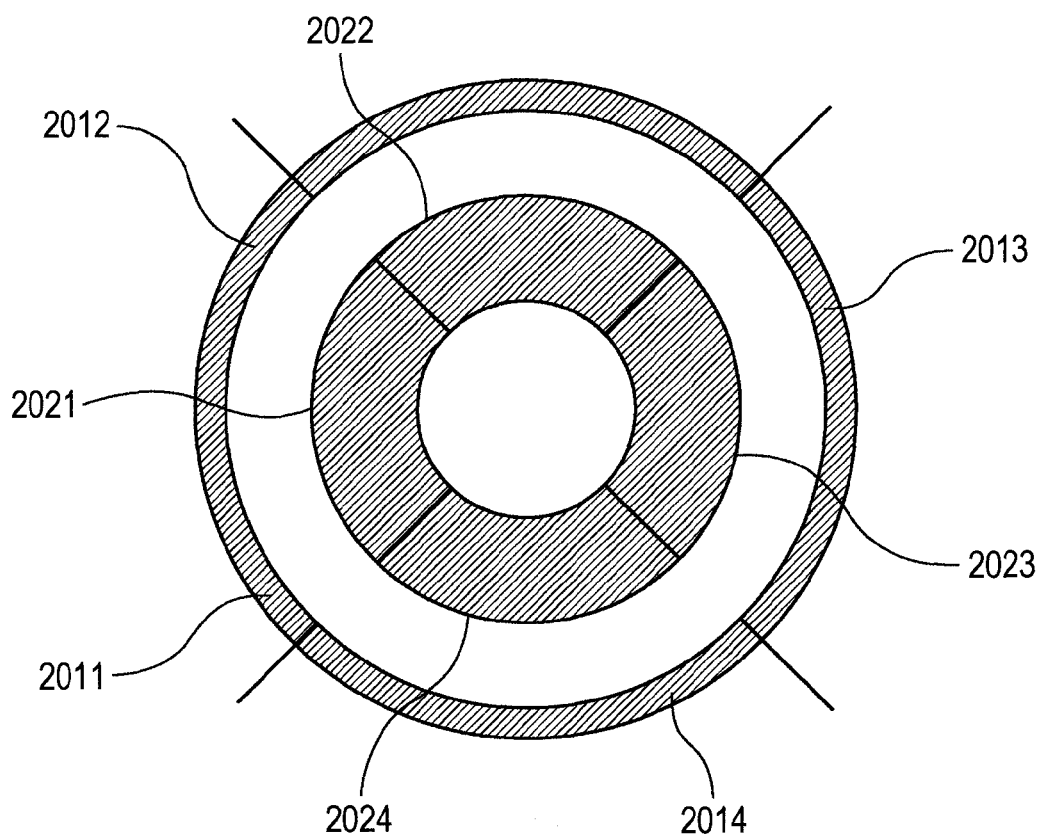
FIG. 2B is a plan view showing the schematic configuration of the illumination system according to the first embodiment.

As shown in FIGS. 2A and 2B, illumination is performed for each direction, such that luminosity on a plane including illumination, the center of the bacterial colony, and an optical axis of the camera may be acquired. When acquiring a detailed shape of the bacterial colony, total eight-time imaging of four-time imaging of the image illuminated by the division light sources 2011, 2012, 2103, and 2014 one by one and four-time imaging of the image illuminated by the division light sources 2021, 2022, 2023, and 2024 one by one by the control of the light control unit 115 is preferable. However, in order to shorten an imaging time, it is preferable that several images are illuminated and imaged at the same time. Meanwhile, in order to shorten the imaging time, for example, total two images of one image illuminating the division light sources 2011, 2012, 2013, and 2014 simultaneously and one image illuminating the division light sources 2021, 2022, 2023, and 2024 simultaneously will be enough.

When directly reflected light is detected, color information of a bacterial colony therearound is lost. In order to discriminate the bacterial colony for each kind, the color information is important. Therefore, we selected an angle at which the directly reflected light is not detected as much as possible in low-angle illumination. The illumination of the low-angle illumination unit 101 is performed at the highest angle, θ at the end of the petri dish and according to an evaluation result, it could be seen that when θ is 45° or lower, the color information may be acquired without an influence of the directly reflected light in most bacterial colonies.

Even in high-angle illumination, illumination is performed at the highest angle, $\theta_2$ at the end of the petri dish and it could be seen that when the angle is over 80°, the medium 150 is inclined by surface tension at the end of the petri dish according to the medium 150 and the medium itself is brightly detected by direct reflection. Therefore, even though the high-angle illumination is the highest-angle illumination, the illumination angle is set not to be over 80°.

Figure 3A:
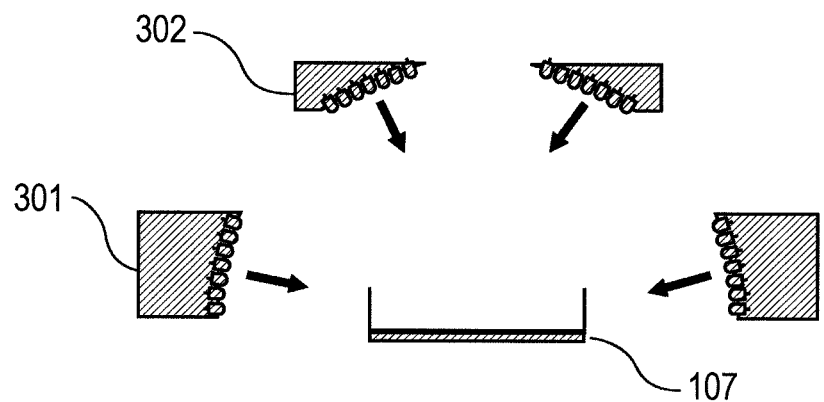
FIG. 3A is a front view showing a schematic configuration of another example of the illumination system according to the first embodiment.
Figure 3B:
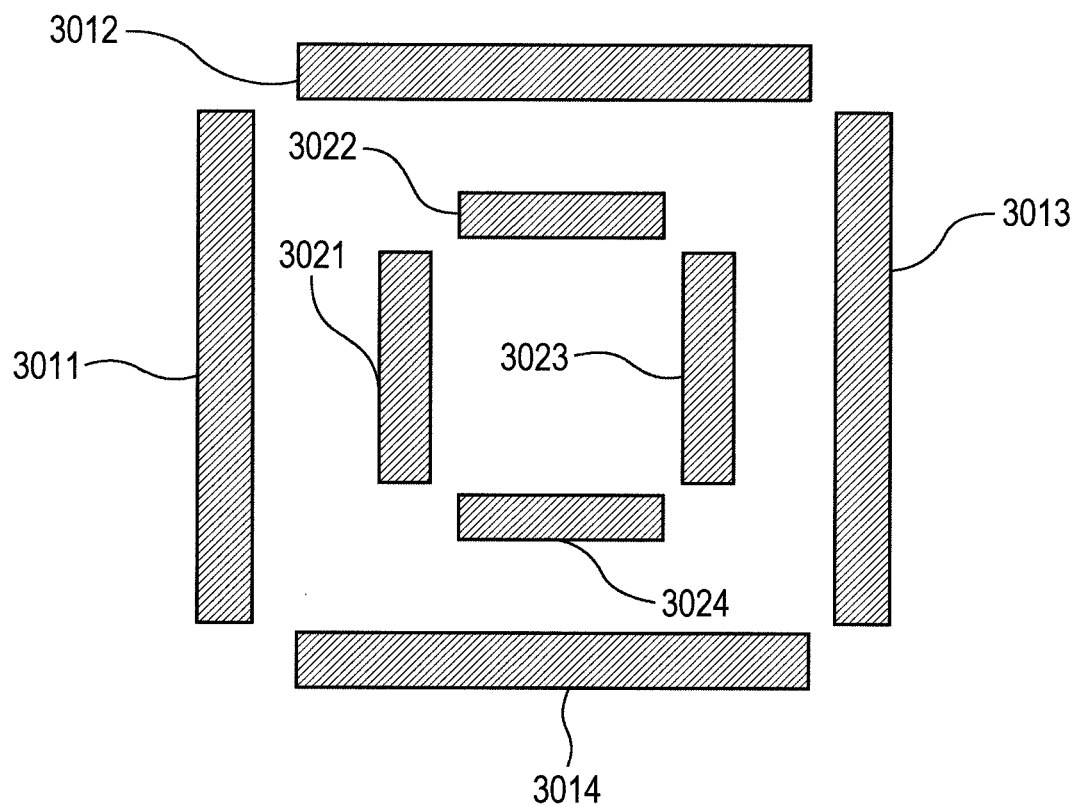
FIG. 3B is a plan view showing the schematic configuration of another example of the illumination system according to the first embodiment.

Since the directly reflected light is not detected in spite of ground illumination from a low angle in most cases in the low-angle illumination formed by the division light sources 2011, 2012, 2013, and 2014 by setting the illumination angle as above, acquired information amount is not large in spite of one-by-one illumination. As a result, the low-angle illumination is preferable in that simultaneous illumination and imaging in all directions shortens the imaging time. In FIG. 3, substantially the same configuration as FIG. 2 is configured by line-shape illumination. Illumination of a low-angle illumination unit 301 is constituted by division light sources 3011, 3012, 3013, and 3014 and illumination of a high-angle illumination unit 302 is constituted by division light sources 3021, 3022, 3023, and 3024. Light-on of the respective light sources may be individually controlled by using the light control unit 115.

Figure 4A:
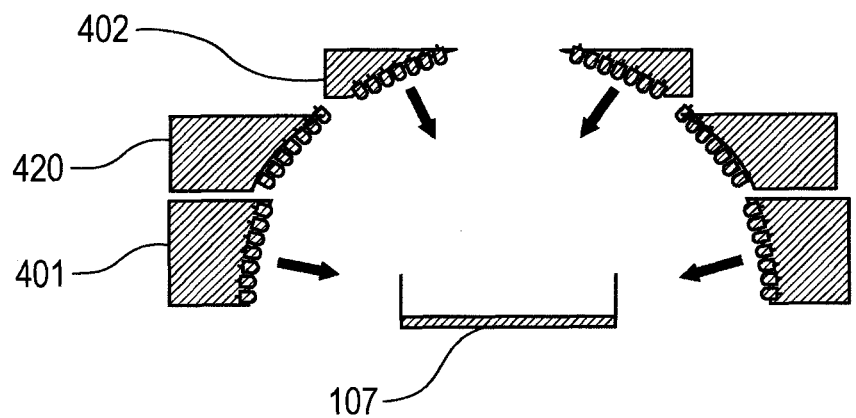
FIG. 4A is a front view showing a schematic configuration of yet another example of the illumination system according to the first embodiment.
Figure 4B:
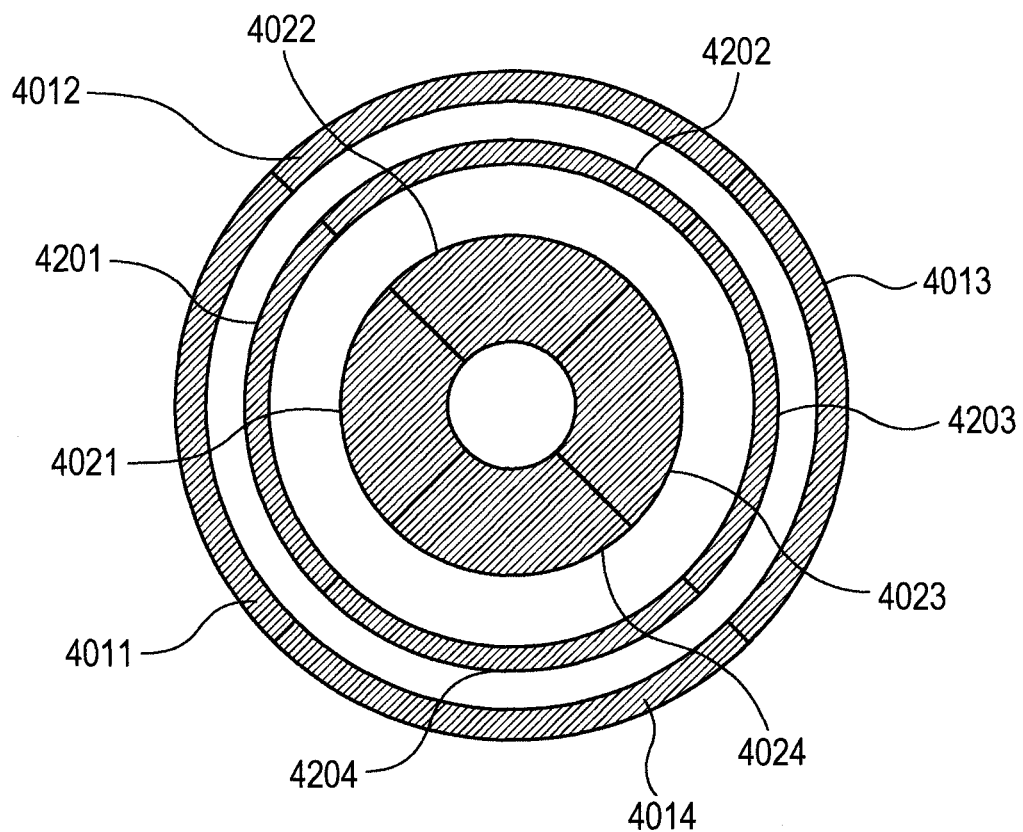
FIG. 4B is a plan view showing the schematic configuration of yet another example of the illumination system according to the first embodiment.

In the configuration of FIG. 2, in order to further increase angle detection resolution, a middle-angle illumination unit 420 may be inserted between a low-angle illumination unit 401 and a high-angle illumination unit 402 as shown in FIG. 4. In this case, illumination of the low-angle illumination unit 401 is divided into four division light sources 4011, 4012, 4013, and 4014, illumination of the high-angle illumination unit 402 is divided into four division light sources 4021, 4022, 4023, and 4024, and illumination of the middle-angle illumination unit 420 is divided into four division light sources 4201, 4202, 4203, and 4204 and light-on thereof may also be individually controlled by using the light control unit 115.

When it is considered that classification is performed based on the directly reflected light of the bacterial colony, the directly reflected light from substantially the same normal direction of the bacterial colony needs to be detected even at any position of the petri dish.

However, the petri dish is, in general, ϕ90 mm and in order to achieve it, the high-angle illumination unit 102, 302, or 402 and the camera 103 need to be significantly separated from the petri dish 107. In order to reduce the separation gap as small as possible, the camera may adopt a telecentric optical system. By this method, a distance between a lens of an imaging system and the petri dish may be shortened.

Figure 17:
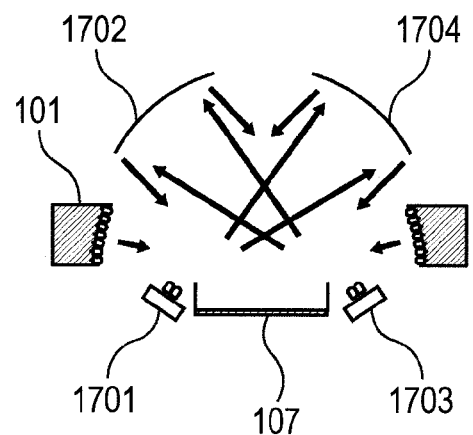
FIG. 17 shows an embodiment of the illumination system of the present invention.

Further, in regard to an illumination system, the high-angle illumination unit 102, 302, or 402 is constituted by a set of a plurality of LEDs, a micro lens is installed in each LED, and a method using comparatively parallel light is adopted, thereby shortening a distance between the positions of the illumination and the petri dish 107. Further, as another configuration, a system shown in FIG. 17 is also used. Reference numerals 1701 and 1703 represent light sources, reference numerals 1702 and 1704 represent parabolic mirrors, and the light sources 1701 and 1703 are placed at focus positions of the parabolic mirrors 1702 and 1704, respectively. By this configuration, light emitted from the light sources 1701 and 1703 to the parabolic mirrors 1702 and 1704, respectively, is reflected on the parabolic mirrors 1702 and 1704 to be parallel light, thereby radiating the petri dish 107. As a result, light may be illuminated from substantially the same direction at a random position on the petri dish 107. Reference numerals 1702 and 1704 may be spherical mirrors instead of the parabolic mirrors, respectively.

Figures 5A, 5B:
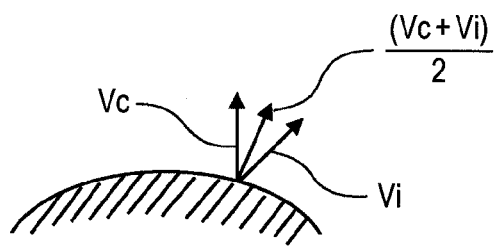
FIG. 5A is a diagram showing a relationship between an illumination condition of an imaged image of a bacterial colony by a detection system and a shape of the bacterial colony according to the first embodiment.
FIG. 5B is a cross-sectional view of the bacterial colony describing a relationship of incident light and reflected light to the bacterial colony by the detection system and a normal line direction on the surface of the bacterial colony according to the first embodiment.

FIG. 5A shows an actualized state of a feature of a bacterial colony by each illumination. In the high-angle illumination, according to the position of reflection light, an angle of the bacterial colony at the position of the reflection light may be acquired. The normal-line direction of the bacterial colony at the position from which the directly reflected light is detected is expressed by (Vc+Vi)/2 by using a unit vector Vc from the position of the reflection light toward the camera lens and a unit vector Vi from the position of the reflection light to the illumination, as shown in FIG. 5B. It may be estimated that, when the bacterial colony is flat, a position where the reflected light is detected is around the center of the bacterial colony and when the position of the reflected light is around the bacterial colony, the bacterial colony has a height from the medium. Further, when the bacterial colony has a shape collapsed from a dome shape, the reflected light is detected at a plurality of positions. On the other hand, in the low-angle illumination, even when a surface shape of the bacterial colony is slightly changed, luminosity is not changed, but color and luminosity information of the surface of the bacterial colony is easily acquired.

Figure 6:
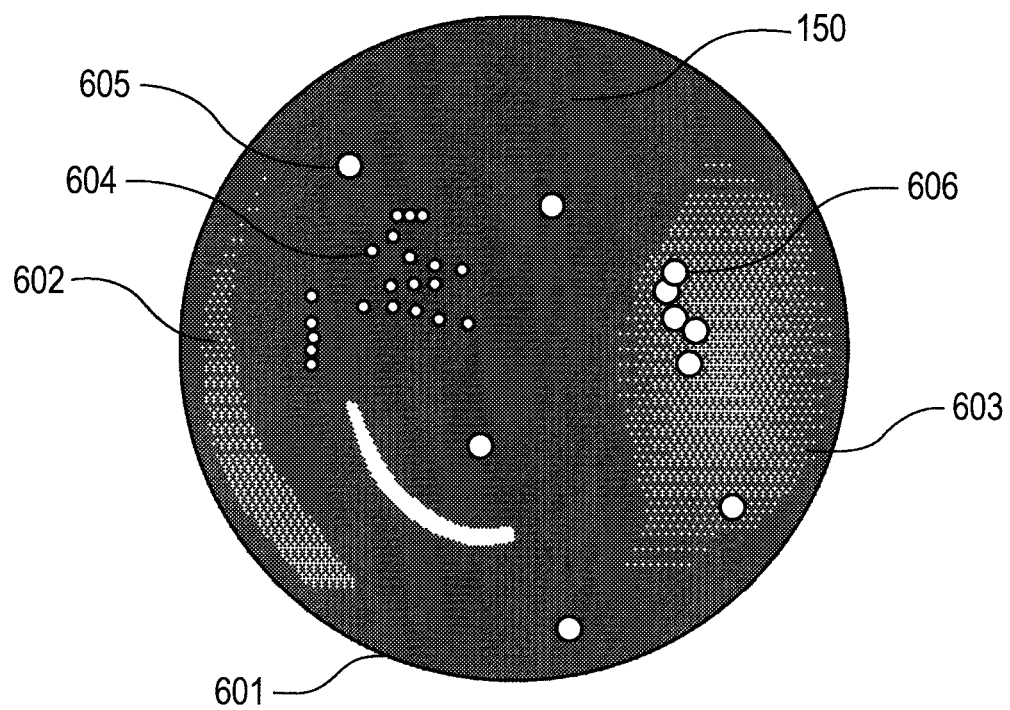
FIG. 6 is the imaged image of the bacterial colony by the detection system according to the first embodiment.

FIG. 6 shows the distribution of the bacterial colonies in the petri dish. Reference numeral 601 represents the petri dish and as shown by reference numeral 602 thereon, there is a slightly bright area near the outside of the petri dish, which is generated as the medium 150 is inclined due to diffused reflection from the petri dish or an influence of surface tension at an edge of the petri dish. An area where the luminosity or color of the medium 150 is changed by a secretory fluid of the bacterial colony is shown by reference numeral 603. Reference numeral 604 represents a small-sized bacterial colony having comparatively low contrast from the medium 150 and reference numeral 605 represents a bacterial colony having high contrast.

An image signal acquired by imaging the petri dish 107 (601) with the imaging means 103 is received by the image processing means 119, and the bacterial colony having high contrast is easily detected. But, the bacterial colony at reference numeral 603 has low contrast and reference numerals 602 and 603 are spaced apart from each other due to a change from average luminosity or a color of the medium 150. When the bacterial colony is detected through a difference in color or luminosity from the average color or luminosity of the medium 150 by the image processing means 119, the area which is not the bacterial colony, such as reference numeral 602 or 603 is also extracted as the bacterial colony under a condition to extract 604. Therefore, in the embodiment, an isolated bacterial colony may be extracted by using three steps below.

(1) removing a low-frequency component which is a feature of reference numeral 602 or 603 by means of a spatial bandpass filter.

(2) acquiring luminosity or color of an area considered as the medium 150 based on local luminosity around a focused area and comparing the acquired luminosity or color with the local luminosity or color and extracting the focused area as a candidate of the bacterial colony when the focused area is different from the area of the medium in the luminosity or color.

(3) evaluating the distribution of the luminosity or the color of the area extracted as the candidate of the bacterial colony and judging a case in which the luminosity distribution is similar to the dome shape as the bacterial colony.

Figure 7:
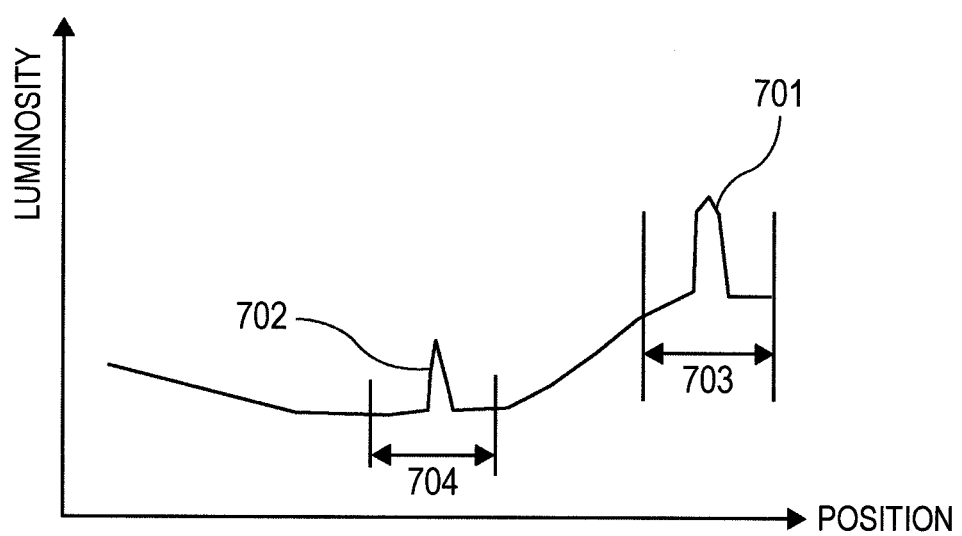
FIG. 7 is a graph showing a luminosity profile of the imaged image of the bacterial colony by the detection system according to the first embodiment.

FIG. 7 shows a way of thinking of an algorithm in step (2). FIG. 7 shows the distribution of luminosity in a 1D direction where an imaged image is present. Reference numerals 701 and 702 represent bacterial colonies to be extracted, but when a simple binarization method is adopted, an area of reference numeral 703 is extracted as the bacterial colony. Therefore, when it is judged whether the area of reference numeral 701 is the bacterial colony, the judgment may be performed based on the area of reference numeral 703 therearound and when it is judged whether the area of reference numeral 702 is the bacterial colony, the judgment may be performed based on an area of reference numeral 704.

As the method of (3), for example, quadratic function fitting may be used. In the processing of (2), even though an area having high luminosity is extracted based on the neighborhood, an area where the plurality of bacterial colonies are overlapped with each other may be extracted as shown by reference numeral 606. In an aggregate of the plurality of bacterial colonies, since the aggregate is not configured by only a single bacterium in some cases, the aggregate should be removed. When transmitted image luminosity of the candidate area of the bacterial colony acquired by (2) is I(x, y), for example, an equation below is calculated in the candidate area of the bacterial colony, coefficients A, B, C, D, E, F, G, and H are calculated by a least-squares method so that Error has a minimum value, and a method using the bacterial colony as the isolated bacterial colony may be adopted only if Error/S is equal to or less than a threshold when an area of the candidate area of the bacterial colony is set as S. Further, the quadratic function fitting may be calculated similarly by Gaussian function approximation.

$$\text{Error} = \Sigma(Ax^2 + Bx + C + Dy^2 + Ey + F + Gxy + H - I(x,y))^2 \quad \text{(Eq. 2)}$$

In the step described by (2), the image of the medium 150 is not steeply changed, but it was assumed that luminosity in the image is steeply changed by only the bacterial colony. However, actually, other changes in luminosity also occur. The biggest problem is a character written on the petri dish. Reference numeral 801 of FIG. 8A(a) represents an image imaged by illuminating the petri dish 107 from the bottom as shown in FIG. 8A(b) with only the transmitted illumination unit 104 shown in FIG. 1, an image 802 of the petri dish 107 of FIG. 8B(a) is an image imaged by illuminating the petri dish 107 at the low angle with the low-angle illumination unit 101, 301, or 401 as shown in FIG. 8B(b), and an image 803 of the petri dish 107 of FIG. 8C(a) is an image acquired by illuminating the petri dish 107 from the top with the high-angle illumination unit 102, 302, or 402 as shown n FIG. 8C(b). The character is the clearest in the image 801 of the petri dish 107 in FIG. 8A(a), but it can be seen that in general, a printed character 805 for checking traceability is implemented on the bottom of the petri dish, in the petri dish 107 used to culture bacteria. In a hospital or an inspection institute, a specimen ID may be written with magic ink in order to distinguish a plurality of similar bacteria culturing petri dishes. As such, there is a case in which the character on the bottom of the petri dish may be clearer than the bacterial colony.

In the image illuminated at the low angle, such as the image 802 of the petri dish 107 of FIG. 8B(a), the printed character 805 is not almost viewed, but may be viewed in the medium 150 (corresponding to a medium 610 of FIG. 6) having very high transparency. The character is less clear in the image 803 of the petri dish 107 in FIG. 8C(a) than in the image 801 of FIG. 8A(a), but the character may be viewed more clearly than in the image 802 of the petri dish 107 in FIG. 8B(a). Reference numeral 804 represents the bacterial colony and reference numeral 805 represents the printed character.

When the petri dish is illuminated from the bottom as in the image 801 of FIG. 8A(a), printing of the printed character 805 blocks light, and as a result, the petri dish is imaged very excellently. In the case of the low-angle illumination of the image 802 of the petri dish 107 in FIG. 8B(a), most of the light is reflected on the surface and does not transmit the medium 150, and as a result, the printed character 805 is barely viewed. Since the image 803 of the petri dish 107 in FIG. 8C(a) is illuminated from the top, light is inputted into the medium 150 rather than at the low-angle illumination and the printed character 805 is clearly viewed. In a case other than the transmitted illumination using the transmitted illumination unit 104, the light shielding plate 105 is provided, such that the character of the image 803 of the petri dish 107 in FIG. 8C(a) is difficult to be seen, but it is hard to be completely invisible. Therefore, in step (2), first, it is necessary to specify printing on the bottom of the petri dish such as the printed character 805 or a recording area such as the character, a label, and the like which becomes obstacle when the luminosity and the color of the medium 150 is recognized by local area processing.

Figure 9:
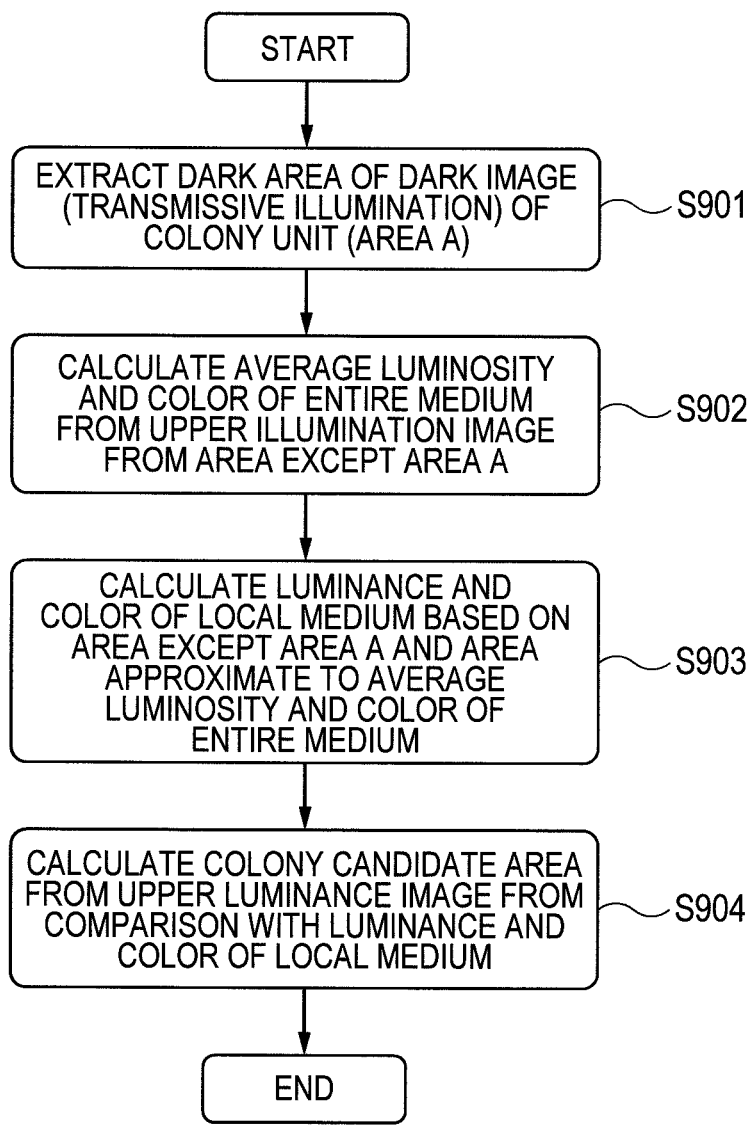
FIG. 9 is a flowchart showing a sequence of extracting a bacterial colony candidate area of bacteria in the first embodiment.

An algorithm of extracting the candidate area of the bacterial colony by specifying and excluding the recording area will be described with reference to FIG. 9. First, a dark area A is extracted from the transmitted illumination image acquired by imaging with the imaging means 103 a transmitted illumination state of the petri dish 107 from the bottom by using the transmitted illumination unit 104 (S901). The dark area A is generally the area of the bacterial colony or the recording area of the bottom of the petri dish. Subsequently, in an area other than the area A, the petri dish 107 is illuminated from the top by using any one of the high-angle illumination unit 102, 302, or 402 and the low-angle illumination unit 101, 301, or 401 or combinations of the plurality of units, and the average luminosity of the medium 150 is acquired from the upward illumination image acquired by using the camera 103 (S902). Herein, the image by the high-angle illumination using the high-angle illumination unit 102, 302, or 402, the image by the low-angle illumination using the low-angle illumination unit 101, 301, or 401, or both sides may be used. The reason is that there is a colony which is apt to be actualized in the image by the high-angle illumination and there is another colony which is apt to be actualized in the image by the low-angle illumination.

The most robust algorithm preferably performs both sides. Furthermore, when illumination is performed for each illumination direction by using the low-angle illumination unit 101, 301, or 401 or the high-angle illumination unit 102, 302, or 402, calculating averaged synthetic images of images sequentially illuminated from all directions, respectively may detect a bacterial colony which does not depend on the position of the petri dish.

In general, even when the medium 150 is discolored by a secretory fluid of the bacteria, the amount of discolor of the medium 150 is not so large. Therefore, subsequently, luminosity and color of the local medium 150 are acquired from an area having brightness and color close to the average luminosity (S903). An area having luminosity and color which are largely different from the local luminosity and color is extracted as the candidate area of the bacterial colony (S904).

Figure 10:
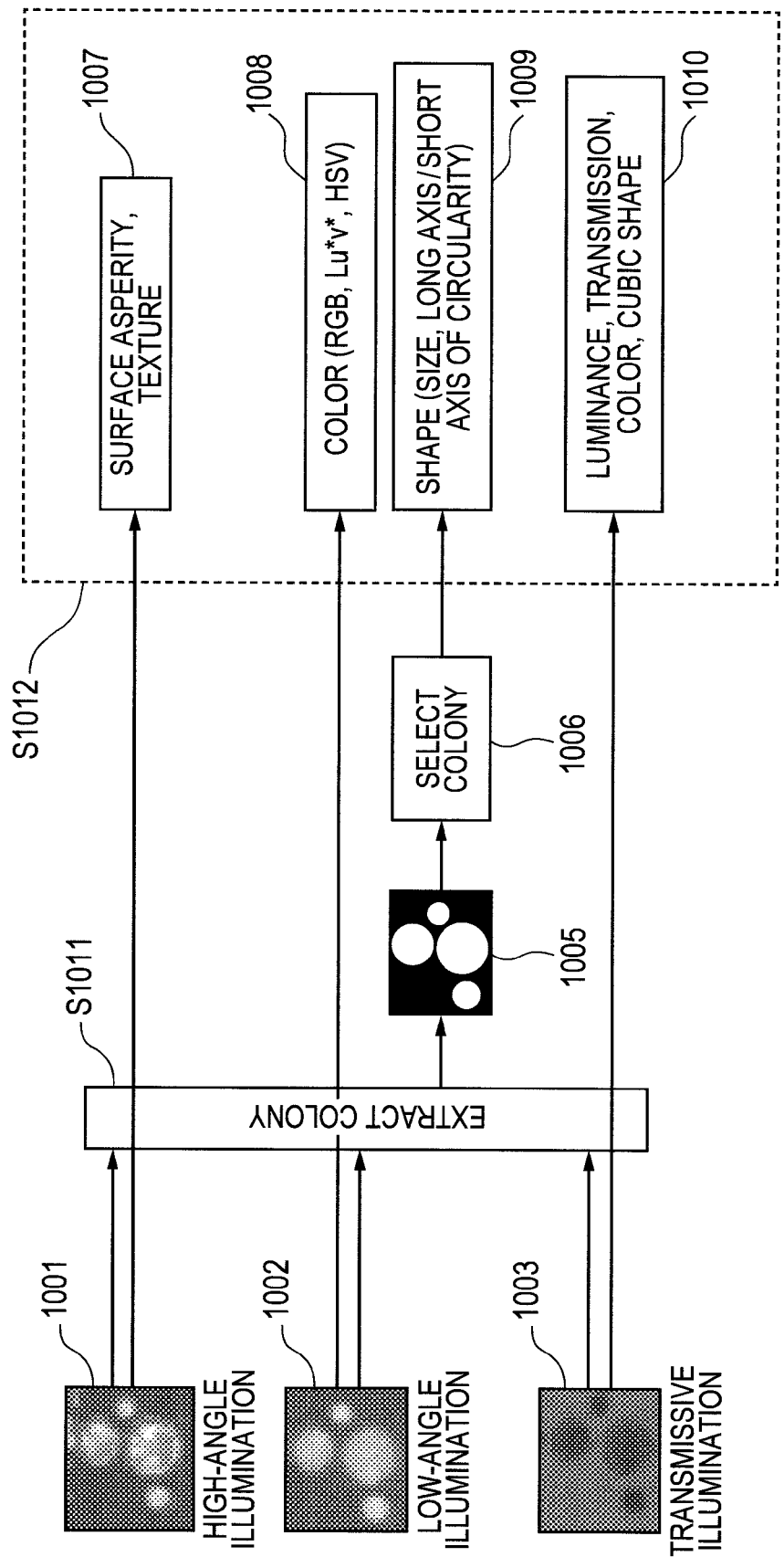
FIG. 10 is a flowchart showing a sequence of extracting an image feature amount of a bacterial colony of bacteria in the first embodiment.

Subsequently, a step of extracting an image feature amount of the bacterial colony from the extracted candidate area of the bacterial colony will be described with reference to FIG. 10. First, a bacterial colony 1005 is extracted from the candidate area of the bacterial colony extracted in S904 of FIG. 9 by using the method described in (3) (S1011). The image feature amount of the bacterial colony for grouping the bacterial colonies is calculated from the area of each extracted bacterial colony (S1012).

As the image feature amount, at least feature amounts described below are calculated by processing a high-angle illumination image 1001 (illuminated by the high-angle illumination unit 102), a low-angle illumination image 1002 (illuminated by the low-angle illumination unit 101), and a transmitted illumination image 1003 (illuminated by the transmitted illumination unit 104). Further, a plurality of high-angle illumination images are sequentially acquired and individually processed by individually illuminating the high-angle illumination image 1001 from the plurality of directions to acquire a feature which has excellent distinctiveness.

(a) Surface Irregularity: 1007

Since a normal direction of a colony at a position where the surface irregularity is observed can be calculated according to the position of the directly reflected light as shown in FIG. 5, the surface irregularity is acquired therefrom.

(b) Texture: 1007

The texture is also acquired from a state in which the directly reflected light is emitted. When the surface becomes rough, the directly reflected light of a small area is observed as a non-point target with respect to the center of the bacterial colony for each direction, and as a result, the texture is used.

(c) Color: 1008

The color feature is calculated from the image acquired by the low angle illumination or the image acquired by the transmitted illumination. The color feature may be auxiliary calculated from the image illuminated at the high angle. As a color space, a Lu*v* space or an HSV space may be used as well as general RGB. In particular, when an RGB image is used in the case where the transmitted illumination image is used, luminosity is changed according to a height of the bacterial colony from the medium 150, and as a result, there is a strong possibility that the feature amounts will not be statistically independent from each other when a height feature and a color feature of the bacterial colony are separately set. As a result, the Lu*v* space or HSV space in which the luminosity and the color are independent has a large merit.

(d) Shape (Size, Circularity, Long Axis/Short Axis): 1009

The size of the area, the circularity thereof, or a long axis/short axis when a shape is elliptically approximated is acquired from the image with respect to the bacterial colony 1006 selected among the detected bacterial colonies 1005. The circularity is acquired by dividing a circumferential length of the area by the square root of an area. By the circularity, an edge of bacteria having an amoeboid form is actualized.

(e) Luminosity, Color, Transmittance, and Cubic Shape: 1010

Figure 11:
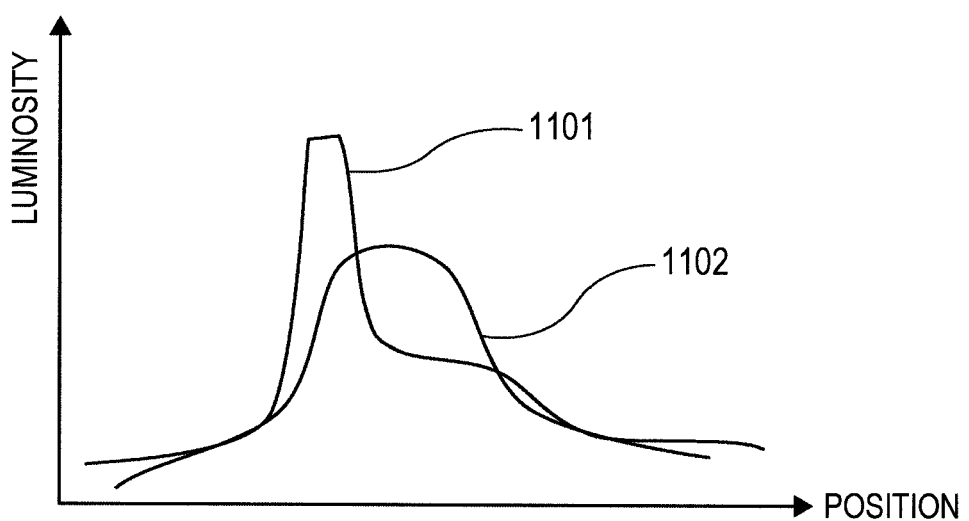
FIG. 11 is a graph showing a luminosity profile of the bacterial colony of the bacteria in the first embodiment.

The luminosity, color, transmittance, and cubic shape are acquired from the transmitted illumination image 1003. The transmittance and the height from the medium 150 can be acquired based on the luminosity and direct reflection of the high-angle illumination image. FIG. 11 shows the relationship between the high-angle illumination image and the transmitted illumination image. Reference numeral 1101 represents a luminosity level at each position of the high-angle illumination image illuminated from any one direction and reference numeral 1102 represents a luminosity level at each position of the transmitted illumination image.

The transmitted illumination may be used only when the medium 150 has high light transmittance and the transmitted illumination becomes dark at the position of the bacterial colony, and as a result, the thickness of the bacterial colony increases and further, becomes dark. When any luminosity in the bacterial colony is set as IC(x, y) and an average value of the luminosity of the medium 150 is set as IM, the thickness D(x, y) of the bacterial colony at a position of (x, y) is acquired by an equation below.

$$D(x,y) = -G(\log IC(x,y) - \log IM) \quad \text{(Eq. 3)}$$

Herein, G represents a gain determined for each bacterial colony species.

It is assumed that the reflected light by the high-angle illumination can be detected at a position (X, Y). In this case, a normal vector is inclined from a vertical direction by $\theta$. In this case, a change in thickness when the position is deviated by $\Delta x$ becomes $-\Delta x \tan \theta$. Herein, when a difference of D(x, y) is calculated as below.

$$D(X+\Delta x, Y) - D(X,Y) = -G(\log\ IC(X+\Delta x, Y) - \log\ IC(X,Y)) = -\Delta x \tan\theta$$

That is, $$G = \Delta x \tan\theta / (\log IC(X+\Delta x, Y) - \log IC(X,Y)) \quad \text{(Eq. 4)}$$

The difference is acquired by Eq. 4, and as a result, the thickness of the bacterial colony is acquired at any position. Therefore, when only a place where the directly reflected light is generated is discovered in the medium 150 having comparatively high transmittance, the place becomes a very important feature amount in identifying the bacterial colony in which the cubic shape and volume are acquired. For example, the maximum height, volume, average height, and outer peripheral height of the bacterial colony are calculated from the information. A vector using the features as components is acquired and the vector is set as the image feature amount of each bacterial colony.

The bacterial colonies are classified into the bacterial colony for each bacterial species in the grouping means 118 by using information of the image feature amount for each bacterial colony acquired by the image processing means 119. The method of classifying the bacterial colonies into the bacterial colony for each bacterial species basically includes two methods. One is a method of classifying the bacterial colonies for each bacterial species which is already registered and the other is a method of classifying the bacterial colonies for each kind of bacterial colony only by the bacterial colony image of the petri dish which is given.

The first method will be described with reference to FIG. 12. Reference numeral 1201 of (a) represents a feature amount database (DB) and the database may search data by using an index 1201 shown in (b). A bacterial species 12021 is not particularly limited to one bacterial species and may be a group consisting of several bacterial species, but even in this case, the bacterial species 12021 is a group consisting of bacterial species having similar appearances. Next, a medium 12022 will be described. The bacterial colony may be limitatively generated by the medium and further, in some media, the color of the bacterial colony is largely changed according to the bacterial species. As a result, information of the medium is very important in classifying bacteria. In the case of a specimen 12023, bacteria which are easily generated are changed depending on whether the specimen acquiring bacteria is, for example, patient's blood, feces, or urine. The information is also important in classifying bacteria in order not to overlook important bacteria. Further, a culturing condition 12024 of the bacterial species 12021 is important in classifying the bacterial species. Last, feature amount data 12025 will be described.

The feature amount data 12025 is vector data and is constituted by a set of vector data of a plurality of same kind of bacterial colonies. For example, reference numerals 1203, 1204, and 1205 shown in FIG. (c) represent vector groups of bacterial colonies of different bacterial species imaged with the same medium, specimen, and culturing condition, respectively. Now, when a feature amount vector acquired from a bacterial colony of a new unknown bacterial species is 1206, the most similar feature amount vector 1205 is adjacent to 1206 in the present invention, and as a result, 1206 is also judged as the same bacterial colony as 1205.

A typical bacterial colony is registered in the database as described above. But there is a case where bacteria cultured from the specimen may not be particularly registered in the database. In order to deal with this case, a method of interactively grouping the feature amount vector acquired from the petri dish by image processing without using the database may be used.

Figure 13A:
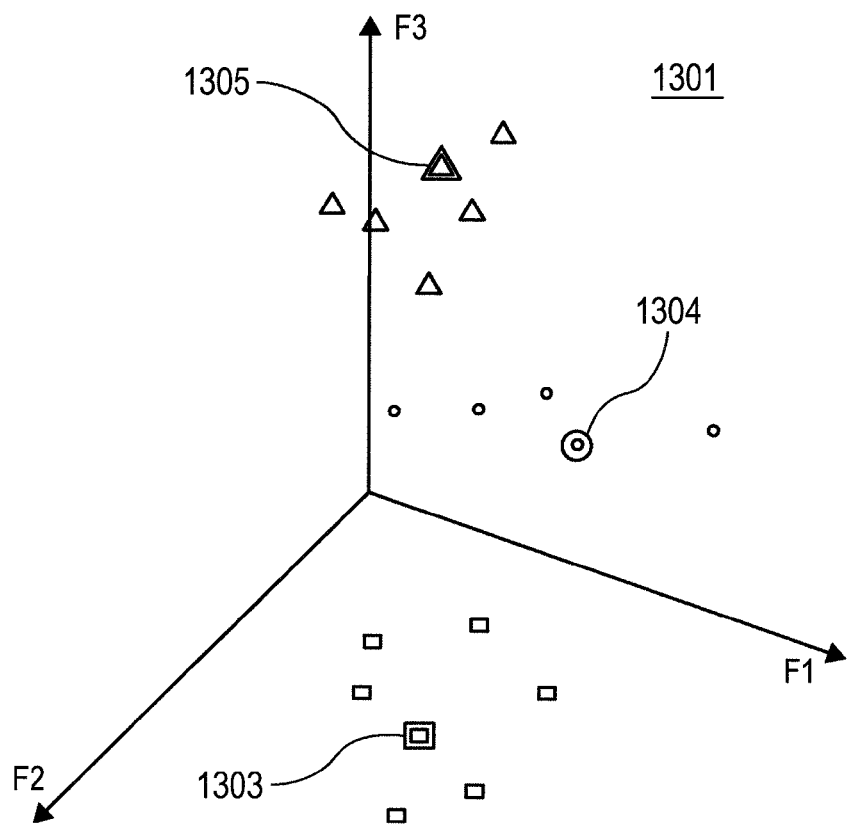
FIG. 13A is a graph showing one example of the distribution in a feature amount space of the bacterial colony of the bacteria in the first embodiment.
Figure 13B:
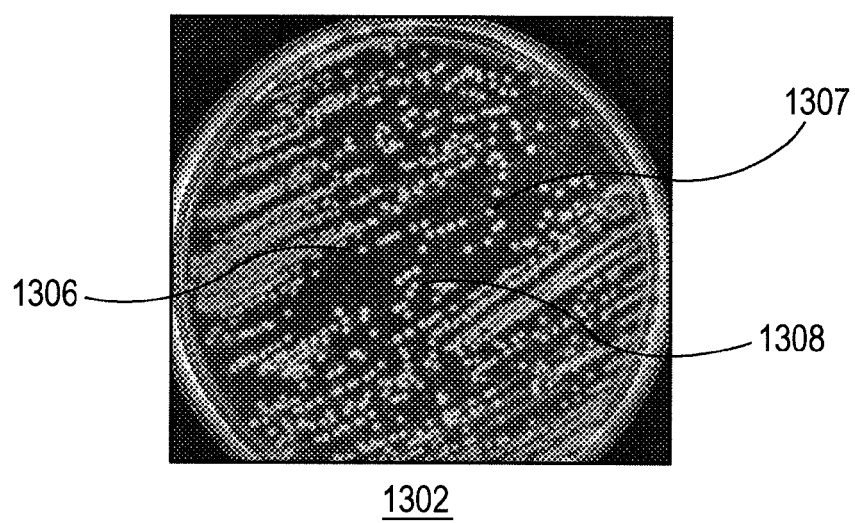
FIG. 13B is an image of the petri dish in which the bacterial colony of the bacteria is distributed in the first embodiment.

This algorithm will be described with reference to FIGS. 13A and 13B. In a feature amount space 1301 of FIG. 13A, reference numerals 1303, 1304, and 1305 represent feature amount vectors of the bacterial colonies which correspond to a bacterial colony 1306, a bacterial colony 1307, and a bacterial colony 1308, respectively in an image 1302 of the petri dish shown in FIG. 13B. When a tester instructs that typical examples of bacterial colonies to be grouped are 1303, 1304, and 1305 to the system while a drawing of the feature amount space shown in FIG. 13A is displayed on the GUI 124 described in the configuration of the entire device of FIG. 1, the grouping means 118 groups the feature amount vectors by using a clustering method which is generally known.

As the clustering method, a method such as, for example, an EM algorithm, k-means, or purge k-means may be used and an instruction result of the tester may be used as an initial grouping state before executing this algorithm. Further, not the clustering algorithm but a general classification algorithm, for example, a nearest neighbor method or a Naive Bayes method may be used. When the classification algorithm is used, the classification algorithm is executed with a class in which samples are instructed one by one.

When the feature amount is largely distant from a feature of a typical bacterial colony instructed by the tester, the grouping means 118 excludes the classification result from grouping as the unknown bacterial colony. Further, bacterial colonies which are equally spaced apart from the feature amount of the plurality of bacterial colonies instructed as the typical bacterial colonies are excluded from grouping as bacterial colonies of which a grouping destination is unclear. This is inevitable in order to prevent tolerance of the drug from being evaluated by using bacteria which is not presented originally, in implementing, for example, the MIC method. Further, the to system selects a sample to be harvested based on the grouping result. When a plurality of bacterial colonies are cultured, the tester preferably selects the bacterial colony to harvest a bacterial colony close to the bacterial colony selected as the typical bacterial colony in terms of the feature amount in the grouping result.

The result processed by the grouping means 118 is displayed on the GUI screen 124 of the input/output terminal 130. The tester verifies the grouping result shown in the GUI 124 and if the grouping result is a preferable classification result or a harvesting result, the tester instructs the system to harvest the bacterial colony according to this result. When the grouping result is insufficient, a bacterial species of a specific bacterial colony is instructed and newly inserted into the system through the GUI. The grouping means 118 adds the bacterial species as new instruction data of, for example, the Naive Bayes method and classifies the added data and shows the grouping result to the tester almost in real time. Besides, the data may be treated as new instruction data of K-NN classification or a group of added instruction data of the tester may be reflected to an initial state of K-means clustering. Further, other known classification algorithm or clustering algorithm may be used and the classification result after adding the instruction data is displayed to the tester to allow the tester to immediately judge whether the classification result is a satisfactory grouping result.

A bacterial colony in which the tester cannot specify the bacterial species is also present. In this case, the tester registers the bacterial species as the bacterial colony in which the bacterial species cannot be specified in the grouping means 118 through the input/output terminal 130. The grouping means 118 specifies, for example, two groups which are the closest in a feature space of the bacterial colony in which the bacterial species cannot be specified and boundary surfaces of the two groups are moved to the centers of the groups, respectively, in order not to group the bacterial colony in which the tester cannot specify the bacterial species.

Further, the grouping result is not limited to be performed by only one petri dish. The reason is that a plurality of wells are placed on the micro plate, all wells may not be filled with bacteria by only one petri dish, and bacteria of one specimen are cultured by a plurality of petri dishes. In this case, the images of the plurality of petri dishes may be simultaneously displayed to allow the tester to verify the images of the plurality of petri dishes and select an instruction sample. Alternatively, one of them is enlarged and displayed on the GUI 124 and the image may be easily switched by operating a mouse, a track ball, or a keyboard of the input/output terminal 130.

In the system of the present invention, imaging is performed under different optical conditions. When the tester does not verify the image under a plurality of optical conditions, the tester may not specify an accurate bacterial species. Therefore, the images under the plurality of optical conditions may be displayed on the GUI 124. The GUI 124 may display an image under a predetermined optical condition on the GUI 124 by operating the mouse, track ball, or keyboard of the input/output terminal 130 or the GUI 124 may display the images under the plurality of optical conditions simultaneously while displaying only some of the images of the respective petri dishes.

As described above, this system performs grouping based on the image feature amount, shows the grouping result to the tester through the GUI 124, and allows the tester to modify the grouping result, thereby making it possible to select the same bacteria colony and apply the MIC method, but an inexperienced tester may not perform accurate grouping by only an appearance of the bacterial colony. Therefore, more detailed analysis is performed except for application of the MIC method. Infrared spectroscopy or Raman spectroscopy is performed as the analysis method. As the bacterial colony to be harvested, bacterial colonies at the center of a feature amount of each grouped bacterial colony and at a boundary of each group are preferably selected.

In the Raman spectroscopy or infrared spectroscopy, it takes a long time to image an image. In particular, in the infrared spectroscopy, since moisture is not generally permeated by light, an analysis target needs to be dried. Therefore, the bacterial colony is put into the base in which the harvested bacterial colony is once analyzed by using 111 and a function to identify one kind of the bacterial colony is provided.

Figure 14:
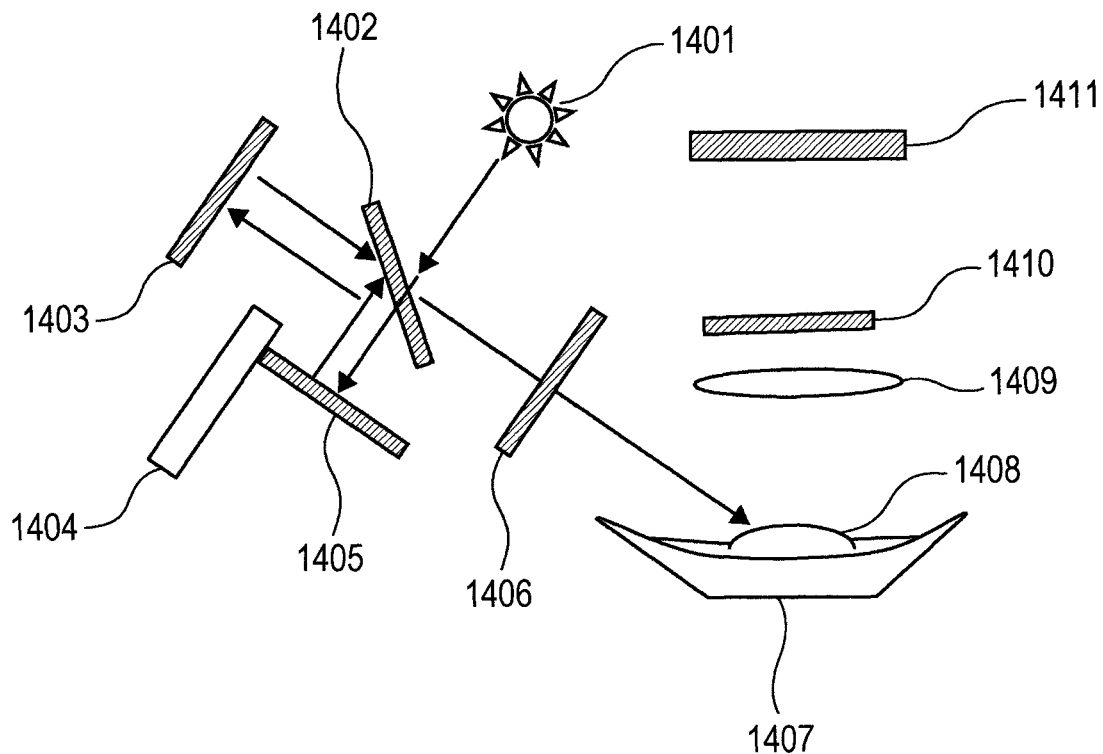
FIG. 14 is a block diagram showing a schematic configuration of an infrared spectroscopic detection system in the first embodiment.

The case using the infrared spectroscopy will be shown in FIG. 14. Reference numeral 1401 represents an infrared light source, reference numeral 1402 represents a half mirror, reference numeral 1403 represents a mirror, and reference numeral 1404 represents a stage and may change the position of a mirror 1405. The stage 1404 is connected with a stage controller 116 and the position of stage 1404 may be controlled by the system. Light reflected on the mirror 1403 interferes with reflected light of the mirror 1405 at the position of the half mirror 1402 and the intensity of the light is changed by a wavelength. Reference numeral 1407 represents a base. Reference numeral 1408 represents a harvested bacterial colony and the light interfered by the half mirror 1402 is radiated to a bacterial colony 1408 after a polarization direction thereof is adjusted to a polarization filter 1406.

A polarization direction of light that transmits the polarization filter 1406 generally becomes P polarization and an illumination angle is set to be approximate to a Brewster angle to control direct reflection from the bacterial colony 1408 to be reduced. Further, even though the angle is not the Brewster angle, polarization directions of a polarization filter 1410 at a detection side and the polarization filter 1406 at an illumination side are perpendicular to each other to suppress the directly reflected light. In the case of a polarization direction of light reflected by the bacterial colony 1408, since a condition to capture most light diffused inside the bacterial colony is changed by a composition of the bacterial colony 1408, the polarization filter 1410 may rotate to adjust a polarization characteristic. Reference numeral 1409 represents a condensing lens. In order to perform only analysis of near-infrared light, a general lens made of quartz may be used and a reflection object lens may be used in order to analyze mid-infrared light.

Reference numeral 1411 represents light detection means. As the light detection means 1411, a photo multiplier tube detecting weak light at a high gain is appropriate and preferably, a photo multiplier tube of a multi anode in which the photo multiplier tube is placed in a 2D shape is appropriate to determine a spatial distribution. Besides, a method of placing an image intensifier on a front surface of a detector and detecting the weak light by using a 2D CCD or CMOS sensor at a rear end may be used and a general CCD sensor or CMOS sensor may be placed.

A detected optical signal is expressed by an equation below.

$$F(X) = \int B(\lambda) \cos(2\pi \lambda X) d\lambda \quad \text{(Eq. 5)}$$

Herein, $B(\lambda)$ is the detected amount of light for each wavelength $\lambda$ of light. X represents an optical path difference between a path reflected on 1403 and a path reflected on 1405, which is generated by controlling the stage 1404. Detected $F(X)$ is transmitted to 117 and $B(\lambda)$ is calculated by Fourier transform based on $F(X)$ for each X.

That is, $$B(\lambda) = \int F(X) \cos(2\pi \lambda X) dX \quad \text{(Eq. 6)}$$

When light is detected by the photo multiplier tube of a multi-anode placed in the 2D shape or the CCD, $B(\lambda)$ is calculated at a position corresponding to each pixel. In general, when a reflection spectrum of light is acquired by the infrared spectroscopy, an absorption coefficient of water is large, such that measurement precision is significantly deteriorated by moisture. For enabling the measurement, as one method, the bacterial colony 1408 is formed in a dried power shape.

As another method, there is a method in which only near-infrared wavelength that less absorbs water is analyzed. When the near-infrared wavelength is analyzed, an absorption strength decreases, and as a result, it is difficult to identify bacteria, but important information is given to discriminate bacteria. When the near-infrared light is used, the bacterial colony 1408 need not be dried, and as a result, moisture may be kept in the base 1407. Therefore, moisture is inputted into the micro plate 123 after measurement to perform the MIC method as it is.

When only the near-infrared light is used without using infrared light, the bacterial colony need not be dried, and as a result, the optical system described in FIG. 14 may be placed directly around the petri dish 114 of the optical system shown in FIG. 1 and the bacterial colony on the petri dish may be directly analyzed.

Figure 15:
FIG. 15 is a graph showing a relationship between a wave number and light absorbance of light in the first embodiment.

FIG. 15 shows a correspondence of a wave number of light and light absorbance. As the light absorbance, the intensity of the light detection means 1411 may be used as it is. But, when the bacterial colony 1408 is not uniform, it is difficult to set the detected amount of light as the light absorbance. In such case, setting a light intensity having a wave number to acquire the maximum amount of light as a reference and a rate of intensity of light detected by each pixel is preferably converted into the light absorbance. The correspondence of the wave number and the light absorbance acquired as above is compared with a correspondence of a wave number and light absorbance already registered in the secondary storage device 125 and bacteria of the same species are extracted. Further, light absorbances of a plurality of bacterial colonies acquired in the same petri dish or the same specimen are compared with each other to discriminate the bacterial species.

According to the embodiment, by using the image acquired by illuminating the petri dish from the top and the image acquired by transmitting and illuminating the petri dish from the bottom, the image of the bacterial colony may be separated from an image of a character or a symbol written or formed on the petri dish to be detected and the bacterial colony species may be classified and accurately harvested by image processing.

By using images illuminated from a plurality of elevation angle directions, it makes possible to more accurately extract the image of the bacterial colony, and further, since the images may be classified by using feature amounts of a plurality of different images in the illumination direction, the bacterial colony species can be classified more accurately. As a result, the bacterial colony species may be classified and accurately harvested automatically without human hands.

Second Embodiment

In the system configuration shown in FIG. 1, as the imaging means, the camera capable of acquiring the 2D-shaped image is used and in this scheme, the optical system tends to be complicated. As another scheme to prevent the complicatedness, a scheme using a detection system as a linear sensor is used. This system may use the camera 103 in the configuration of FIG. 1 as the linear sensor. In this case, a pulse of the integral multiple of a control pulse of the stage 116 is set as an external synchronization signal of the linear sensor, such that an image in which a magnification is not changed with respect to a driving direction of the stage can be acquired. However, in order to independently acquire the illumination images of the low-angle illumination unit 101, the high-angle illumination unit 102, and the transmitted illumination unit 104, the illumination should be switched and the stage should be operated in each switching, which is disadvantageous in terms of throughput.

Figure 16:
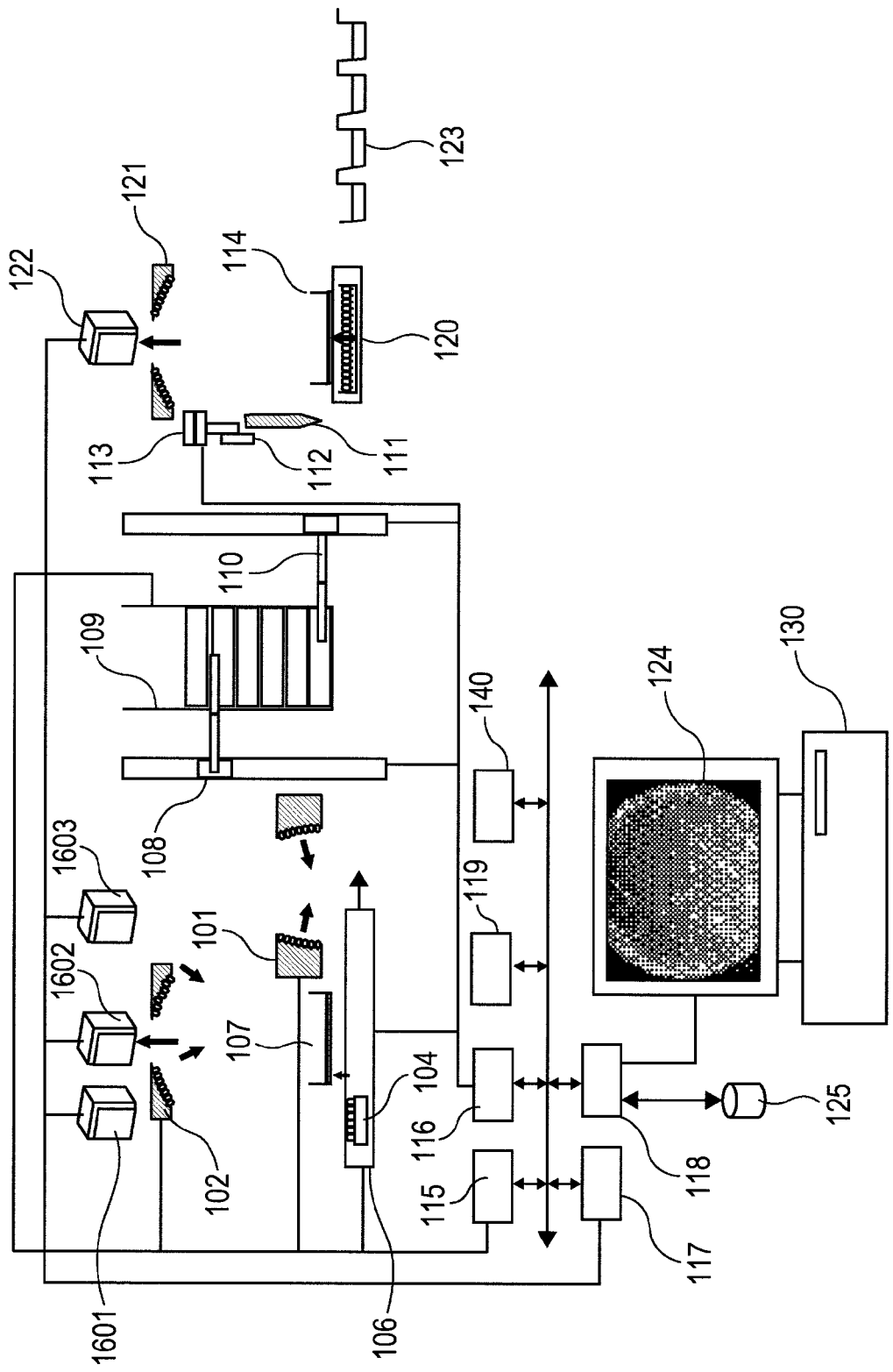
FIG. 16 is a block diagram showing a schematic configuration of an entire system according to a second embodiment.

An embodiment for solving the problem is shown in FIG. 16. In FIG. 16, the same reference numerals refer to the same elements described in FIG. 1. Herein, in the to configuration shown in FIG. 16, linear sensors 1601, 1602, and 1603 are installed instead of the camera 103 of FIG. 1. By setting external synchronization of the linear sensors as the integer multiple of the control pulse of the stage 116, the image in which the magnification is not fluctuating can be acquired. The linear sensor 1601 images the transmitted illumination image by the transmitted illumination unit 104, the linear sensor 1602 images the high-angle illumination image by the high-angle illumination unit 102, and the linear sensor 1603 images the low-angle illumination image by the low-angle illumination unit 101.

Third Embodiment

Hereinafter, a third embodiment of the present invention will be described in detail. However, the present invention is not limited to the embodiment described herein.

(Configuration of Device for Harvesting Bacterial Colony)

Figure 18:
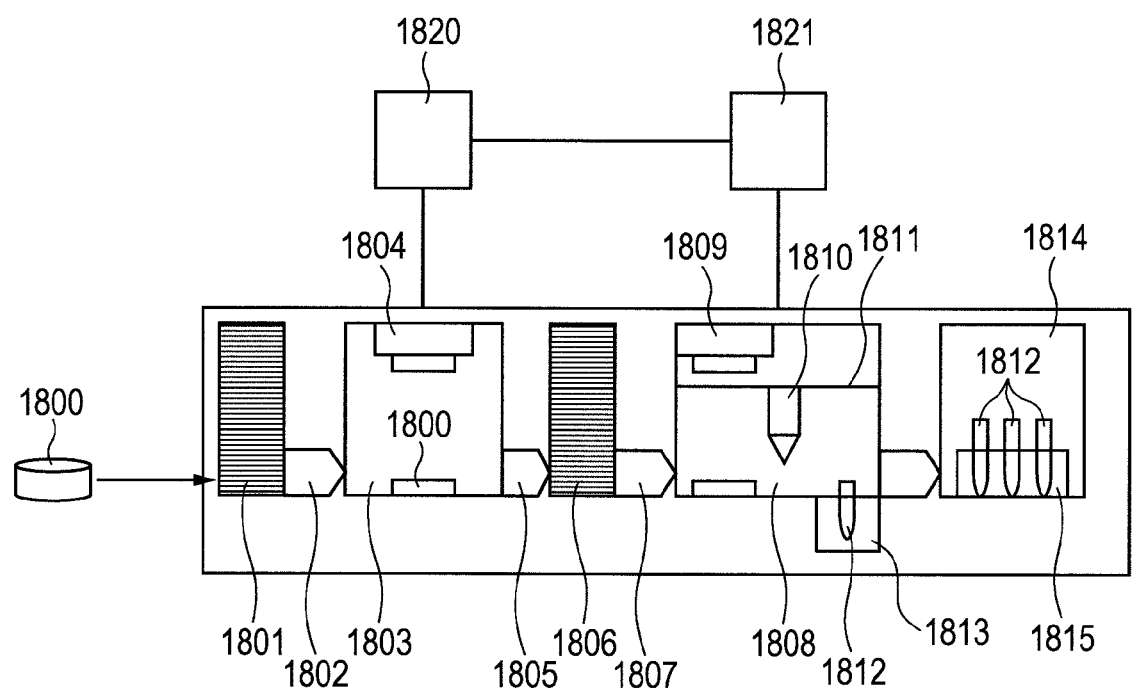
FIG. 18 is a schematic diagram showing one example of a device for harvesting a bacterial colony according to the present invention.

FIG. 18 is a schematic diagram showing one example of a device for harvesting a bacterial colony according to a third embodiment. First, in order to verify whether the microorganism (bacteria) is present in the specimen collected from a patient, the specimen is applied to the agar medium within a petri dish 1800 and inputted into an incubator to culture the microorganism (bacteria) within the petri dish. The culturing is generally performed for 12 hours or more. When the microorganism (bacteria) is present in the specimen, the bacterial colony is generated in the petri dish 1800 by the microorganism after culturing.

The petri dish 1800 in which the bacterial colony is grown is set in a first buffer station 1801. A structure of the first buffer station 1801 is not particularly limited, but a plurality of stages may be installed and the plurality of petri dishes may be stored in a vertical direction, and if a space is permitted, the petri dishes may be spread and stored in a horizontal direction. The petri dishes 1800 set in the first buffer station 1801 are one by one transported to an imaging stage 1803 by first transportation means 1802. An identification code for discriminating each petri dish is preferably provided in each petri dish. As an identifier, a barcode label may be attached to the petri dish in advance and read and in the first buffer station 1801, an identification code corresponding to the position to store each petri dish 1800 may be inputted into a control unit 1802 before being set in the device for harvesting the bacterial colony.

The petri dish 1800 transported to the imaging stage 1803 stops at a position directly below a camera 1804 for imaging an image of the petri dish 1800. In general, in order to avoid water droplets attached to the inside of a cover from dropping, the petri dishes is treated with the cover formed downward and the bottom surface formed upward. In the petri dish 1800, the cover is preferably separated by reversing the petri dish 1800 up and down so that the bottom surface is formed downward in the middle of a transportation path until the petri dish 1800 stops at the position directly below the camera 1804. The image of the petri dish 1800 is acquired by using the camera 1804. Since the image can specify the position of the bacterial colony, the image is imaged with required resolution (in general, approximately 0.1 mm). In the case where desired resolution is not acquired when the image of the entire petri dish is acquired, the image may be imaged by moving the stage 1803 to which the petri dish 1800 is fixed or the camera 1804 and increasing an imaging magnification. One petri dish image or one petri dish image in which a plurality of images are synthesized is acquired.

The imaged image is stored in storage means (memory) within the control unit 1820. Thereafter, bacterial colonies in the petri dish are automatically detected by using the imaged petri dish image and a bacterial colony to be harvested is selected by selection means that selects some of the detected bacterial colonies. A coordinate of the selected bacterial colony is given by an original point and a coordinate axis determined within the petri dish and stored in a storage unit. The selection means and the coordinate allocation method will be described below in detail. The petri dish 1800 in which storing the coordinate of the bacterial colony to be harvested is completed is transported to a second buffer station 1806 by second transportation means 1805. In the second buffer station 1806, the plurality of stages may be installed and the plurality of petri dishes may be stored in the vertical direction, and if the space is permitted, the petri dishes may be spread and stored in the horizontal direction, as in the first buffer station 1801. Herein, when there is a spatial limit, the first buffer station 1801 and the second buffer station 1806 may be commonly used. In this case, for example, the petri dishes imaged from the bottom of the petri dishes stacked the buffer station are sequentially extracted and when imaging and predetermined processing are completed, the petri dishes may be managed without changing the order of the stacked petri dishes by sequentially stacking the petri dishes on the top of the stacked petri dish. By this configuration, one buffer station may serve as two buffer stations.

Subsequently, the petri dishes stored in the second buffer station 1806 are transported to a harvesting stage 1808 by third transportation means 1807. The imaging stage 1803 and the harvesting stage 1808 are installed in different areas. They may be independently operated. The harvesting stage 1808 includes image displaying means 1809, a harvesting tool 1810 including a driving unit capable of moving in X, Y, and Z axis directions, a rail 1811 of the harvesting tool, a test tube 1812, a bacterial liquid concentration adjusting system 1813, and an image outputting device 1821. The image outputting device 1821 reads the image of the petri dish imaged by the imaging stage, from the storage means of the control unit 1820. Further, the image of the petri dish is displayed by the image display means 1809. The displayed images and the imaged images are compared by comparison means within the image outputting device. The original point and the coordinate axis of the petri dish of the imaged image, and the coordinate of the bacterial colony to be harvested are read from the storage means and matched with the position of the displayed image, and a target bacterial colony is harvested. The comparison means of the imaged image and the displayed image will be described below in detail.

After harvesting, the bacterial colony is inputted into the test tube 1812 and the concentration thereof is adjusted to a desired concentration by using the bacterial liquid concentration adjusting system 1813. The concentration is adjusted by increasing or decreasing the quantity of the bacterial colonies or the amount of solvent (for example, normal saline). The test tube 1812 where the adjustment of the concentration is completed is mounted on a suspension rack 1815 of a suspension discharging system 1814 and appropriately carried out outside the device.

The imaging stage 1804, the harvesting stage 1808, the first buffer station 1801, the second buffer station 1806, the first transportation means 1802, the second transportation means 1806, and the third transportation means 1807 are automatically controlled by the control unit 1820.

In FIG. 18, the control unit 1820 and the image outputting device 1821 have different housings and may be integrated with each other.

(Method for Acquiring Coordinate of Bacterial Colony)

Figure 19:
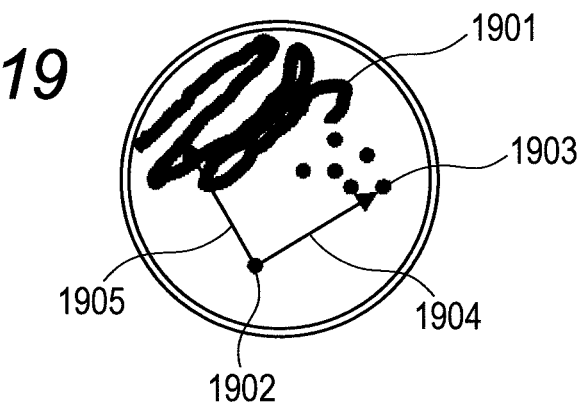
FIG. 19 is a plane schematic diagram showing one example of the image of the bacterial colony in the petri dish.

Subsequently, a method for acquiring the coordinate of the bacterial colony will be described. FIG. 19 is a plane schematic diagram showing one example of the image of the bacterial colony in the petri dish. When the microorganism is included in the specimen, consecutive non-isolated bacterial colonies 1901 are verified in the culturing medium, after culturing. From the image of the petri dish shown in FIG. 19, the original point of the coordinate is defined by image processing and the coordinate of the bacterial colony is acquired. One example of an image processing method will be described below, but the present invention is not limited thereto.

An outer periphery (circle) of the petri dish is acquired by image processing and a central position and a radius thereof are acquired. The bacterial colony within the outer periphery of the petri dish is extracted by contour detection. In the contour detection, a filter that detects a contour, such as a high pass filter, a sobel filter, or the like may be used. A bacterial colony having a diameter in the range of 0.1 mm to 2 mm is selected from the contour of the acquired bacterial colony, and further, a bacterial colony positioned at a leftmost side of a screen is called a bacterial colony A1902 and a bacterial colony positioned at a rightmost side is called a bacterial colony B1903, and the center of an area within each contour is acquired. The center of the bacterial colony A1902 is set as the original point of the coordinate and a direction toward the center of the bacterial colony B1903 from the original point of the coordinate is defined as an X coordinate axis 1904. A Y coordinate axis 1905 is defined in a direction to rotate in a counterclockwise direction from the X coordinate axis 1904 by 90°. After the coordinate axes are determined, the center of each bacterial colony in the screen is acquired and respective coordinates are acquired and written in the control unit 1820 together with the identification code and the petri dish image of the petri dish.

Figure 20A:
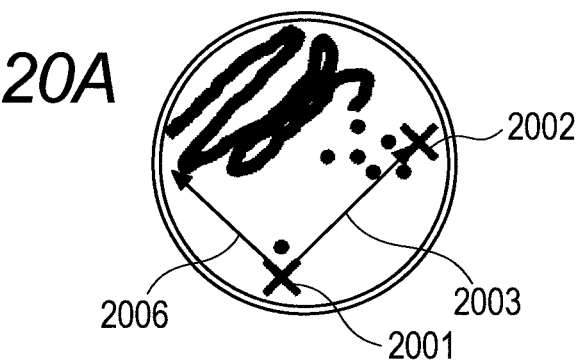
FIG. 20A is a plan schematic diagram showing one example of the image of the bacterial colony in the petri dish.
Figure 20B:
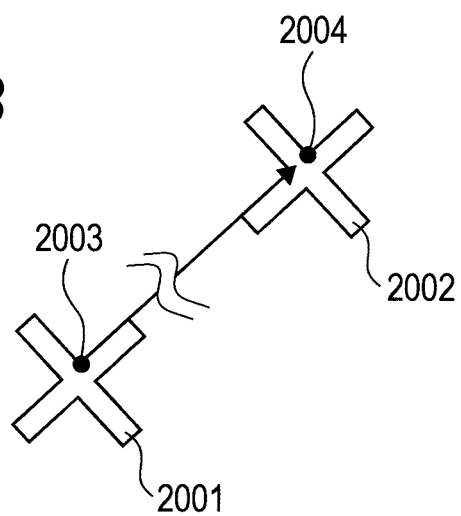
FIG. 20B is a partially enlarged plan schematic diagram of neighboring regions of a marker of FIG. 3-A.

Subsequently, another method will be described. FIG. 20A is a plane schematic diagram showing one example of the image of the bacterial colony in the petri dish. Cross-type markers C2001 and D2002 which are alignment targets are added to the petri dish in advance. As described in FIG. 19, the markers are also detected by the contour detection of the bacteria colony. FIG. 20B is a partially enlarged plan schematic diagram of neighboring regions of the markers of FIG. 20A. A center point of a cross of the marker C2001 is called a starting point 2003 and set as the original point of the coordinate. A center point of a cross of the marker D2002 is called an ending point 2004. A line that links the starting point 2003 of the marker C and the ending point 2004 of the marker D is called an X coordinate axis 2005 and a Y coordinate axis 2006 which is perpendicular thereto is defined. After the coordinate axes are determined, the center of each bacterial colony in the screen is acquired and respective coordinates are acquired and written in the control unit 1820 together with the identification code and the petri dish image of the petri dish.

A shape of the marker is not particularly limited so long as one point thereof may be primarily defined. A shape such as a cross shape, a rectangular shape, a triangular shape, or an I shape may be used. Further, the marker may be printed directly in the petri dish and stamped in the petri dish. In manufacturing the petri dish, a pattern of the marker may be installed in a frame for resin-molding the petri dish and the petri dish having the marker may be fabricated. The marker may be attached to the petri dish by using a seal. Further, when the marker is fabricated on the bottom of the petri dish, the bacterial colony is grown on a medium having a thickness, and as a result, when the heights of the marker and the bacterial colony are different from each other, there is a possibility that both sides cannot be focused simultaneously. In the case of the imaging system considering a focus depth, the seal of the marker made of a resin film may be attached onto the surface of the medium. Since the original point and the coordinate are defined after imaging, positional precision of the marker is available.

The marker may be installed in the petri dish before being inputted into the harvesting device of the bacteria colony and may be installed inside the device.

(Selection Means)

Subsequently, a selection means of a bacteria colony to be harvested will be described. In the imaging stage 1803, the image of the bacterial colony and the coordinate of the bacterial colony are stored in the storage means within the control unit 1820 and thereafter, an operator reviews the images. The operator views the bacterial colony displayed on the screen and selects the bacterial colony to be harvested. As a method for the selection, for example, the bacterial colony may be selected by moving a mouse cursor on the screen and may be selected by displaying the bacterial colony on a touch screen and touching the bacterial colony on the screen. After the operator selects the bacterial colony, the harvesting device of the bacterial colony performs contour detection of the bacterial colony and stores the center of the contour as the coordinate of the bacterial colony to be harvested through the control unit 1820.

(Comparison Means)

Subsequently, in the harvesting stage, a method for detecting and harvesting the bacterial colony selected by the operator will be described. When the petri dish is transported to the harvesting stage, the image of the petri dish 1800 is acquired by the image displaying means 1809 and displayed on the image outputting device 1821. Further, the identifier of the petri dish 1800 is verified and the imaged image of the petri dish stored in the storage means within the control unit 1820 is read to the image outputting device 1821. The contour detection of the image of the petri dish acquired by the image displaying means is performed and the imaged image and the displayed image are compared with each other by the comparison means within the image outputting device 1821. When the petri dish is set in the buffer station or transported by the transportation means, the position thereof is deviated, such that the imaged image and the displayed image may be misaligned in a rotational direction. When the bacterial colony is used as the original point of the coordinate, the original point of the coordinate may not be acquired through the same rule with respect to the imaged image and the displayed image which is inclined at a predetermined rotational angle. The reason is that as the displayed image rotates, the bacterial colony at the leftmost side and the bacterial colony at the rightmost side are different from each other. When the bacterial colony is set as the original point of the coordinate, the displayed image is virtually rotated on the memory several times while the center of the petri dish acquired from the contour of the petri dish is set as the rotational center. In addition, a rotational position of the displayed image is matched by pattern matching and the original point of the coordinate is calculated in that state. When the original point of the coordinate is determined, the coordinate of the bacterial colony which is stored is read and the harvesting tool 1810 including the driving unit moves to the position of the coordinate of the bacterial colony from a newly determined original point of the coordinate to harvest the bacteria.

Coordinate correction or correction of distortion of the coordinate such as parallel movement, enlargement, contraction, and the like may be performed with respect to the displayed image in addition to rotatable movement by the comparison means.

Figure 21:
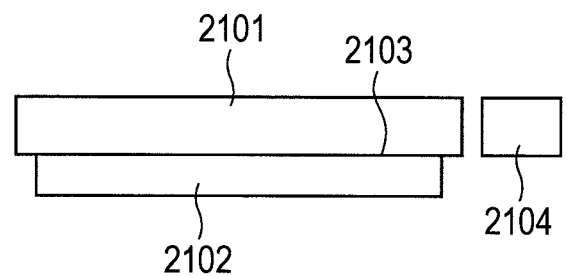
FIG. 21 is a cross-sectional schematic diagram showing a petri dish, a rotational stage, and a photo sensor.

Further, a marker for correcting the rotational angle may be installed in the petri dish instead of calculating a correlation with the image of the petri dish by virtually rotating the displayed image. FIG. 21 is a cross-sectional schematic diagram showing a petri dish, a rotational stage, and a photo sensor. A rotational-direction alignment marker 2103 is installed on a side 2101 of the petri dish. The marker may be installed by methods such as, for example, printing, stamping, molding, attachment, and the like of a line-shaped record. The imaging stage has a rotational stage 2102 on the same axis as the center of the petri dish and a photo sensor 2104 detecting the marker 2103 on the side is installed at a circumferential portion thereof. After the petri dish is set in the stage, the stage stops at a position where the photo sensor 2104 detects the marker 2103 by rotating the rotational stage 2102 and images the image. Similarly, the harvesting stage also includes the rotational stage and the photo sensor and a relationship between a position where the photo sensor is detected and the position of the camera coincides with the position of the imaging stage. When the stage stops at the position where the photo sensor detects the marker 2103 by rotating the petri dish on the stage and images the image, the imaged image and the displayed image which are not misaligned in the rotational direction may be acquired.

(Harvesting Means)

As shown in FIG. 18, the harvesting tool moves on a rail 1811 to move onto the bacterial colony where the petri dish is harvested to harvest the bacteria and the petri dish moves directly below the harvesting tool to harvest the bacteria.

According to the harvesting device of the bacterial colony according to the present invention, harvesting may start sequentially from the petri dish of which imaging is completed in the imaging stage. Accordingly, since imaging and harvesting may be performed in parallel, throughput can be improved.

Figure 22:
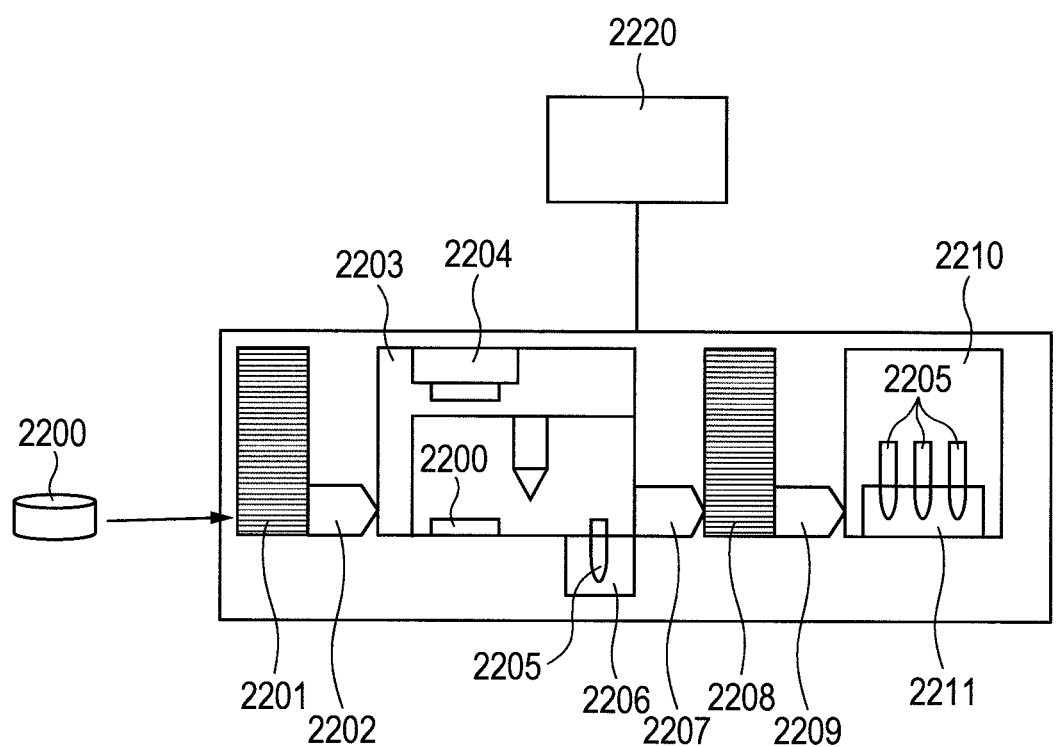
FIG. 22 is a schematic diagram showing another example of a device for harvesting a bacterial colony according to the present invention.

FIG. 22 is a schematic diagram showing another example of a device for harvesting a bacterial colony according to the present embodiment. In a configuration of the device of FIG. 22, the imaging stage and the harvesting stage are placed in a common area. Similarly as the case of FIG. 18, they may be independently operated. The image is imaged and displayed by using an imaging and displaying camera 2204. A control unit 2220 controls an imaging and harvesting stage 2203, a first buffer station 2201, a second buffer station 2208, a first transportation means 2202, a second transportation means 2207, and the imaging and displaying camera. Further, the control unit 2220 includes the storage means storing the imaged image, the selection means selecting the bacterial colony to be harvested from the imaged image, and the comparison means comparing the imaged image and the displayed image.

In the harvesting device of the bacterial colony of FIG. 22, since the petri dish of which imaging is completed or the petri dish of which harvesting is completed may be stored in the buffer station, analysis efficiency can be increased. For example, imaging is performed during break or night when the operator is not present and the petri dish after imaging is stored in the buffer station. The operator selects the bacterial colony to be harvested by using the selection means after the break is completed or a work of the next day starts. Harvesting starts sequentially from the petri dish in which the bacterial colony is selected and the petri dish of which harvesting is completed is also stored in the buffer station. When the device shown in FIG. 22 is used as described above, analysis throughput can be improved because a wait time of the work is not made. Further, since the imaging stage and the harvesting stage are integrated with each other, the device may be simply configured as compared with the device of FIG. 18 and an effect of miniaturizing the device and reducing cost can be acquired.

As described above, according to the harvesting device of the bacterial colony according to the present invention, since imaging and harvesting the image may be processed in parallel, analysis can be efficiently performed without waiting time for processing even when hundreds of specimens are processed.

Fourth Embodiment

Figure 23:
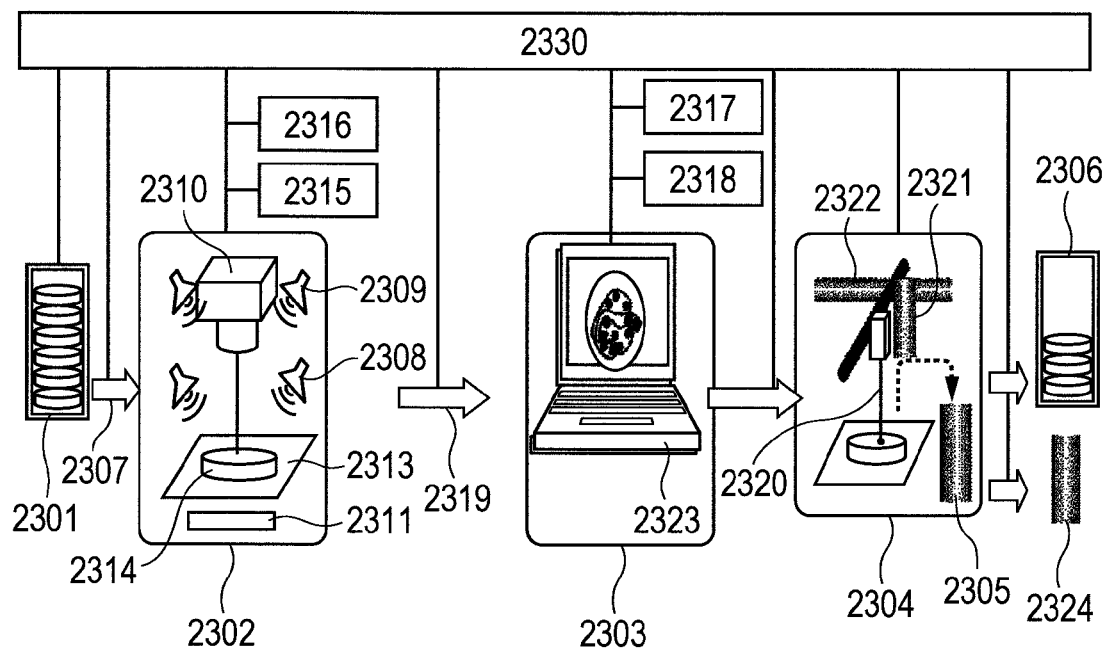
FIG. 23 is an operational principle of a device for harvesting a bacterial colony showing an embodiment based on the present invention.

FIG. 23 shows one example of a device for harvesting a bacterial colony in a fourth embodiment. Prior to using the device in the present embodiment, specimens such as sputum, urine, pus, and the like collected from a patient are applied to the agar medium and separately cultured, and the bacterial colony is formed. A predetermined amount of culture solution in a blood culture vessel, which is judged to be positive is collected and inoculated into a new culture medium and after culturing, the bacterial colony may be formed. In most cases, the bacterial colony may be acquired through culturing for one day (approximately 12 to 18 hours). Reference numeral 2301 represents a petri dish supply stacker, reference numeral 2302 represents a bacterial colony imaging unit, reference numeral 2303 represents an image processing unit, reference numeral 2304 represents a bacterial colony harvesting unit, reference numeral 2305 represents a bacterial liquid preparing unit, and reference numeral 2306 represents a discharge stacker. The petri dish is set in the petri dish supply stacker 2301 where the bacterial colony is grown, transported to the imaging unit 2302 by the transportation means 2307, and set at predetermined positions suitable for imaging with respect to illumination units 2308, 2309, and 2311, and a camera 2310.

Figure 24:
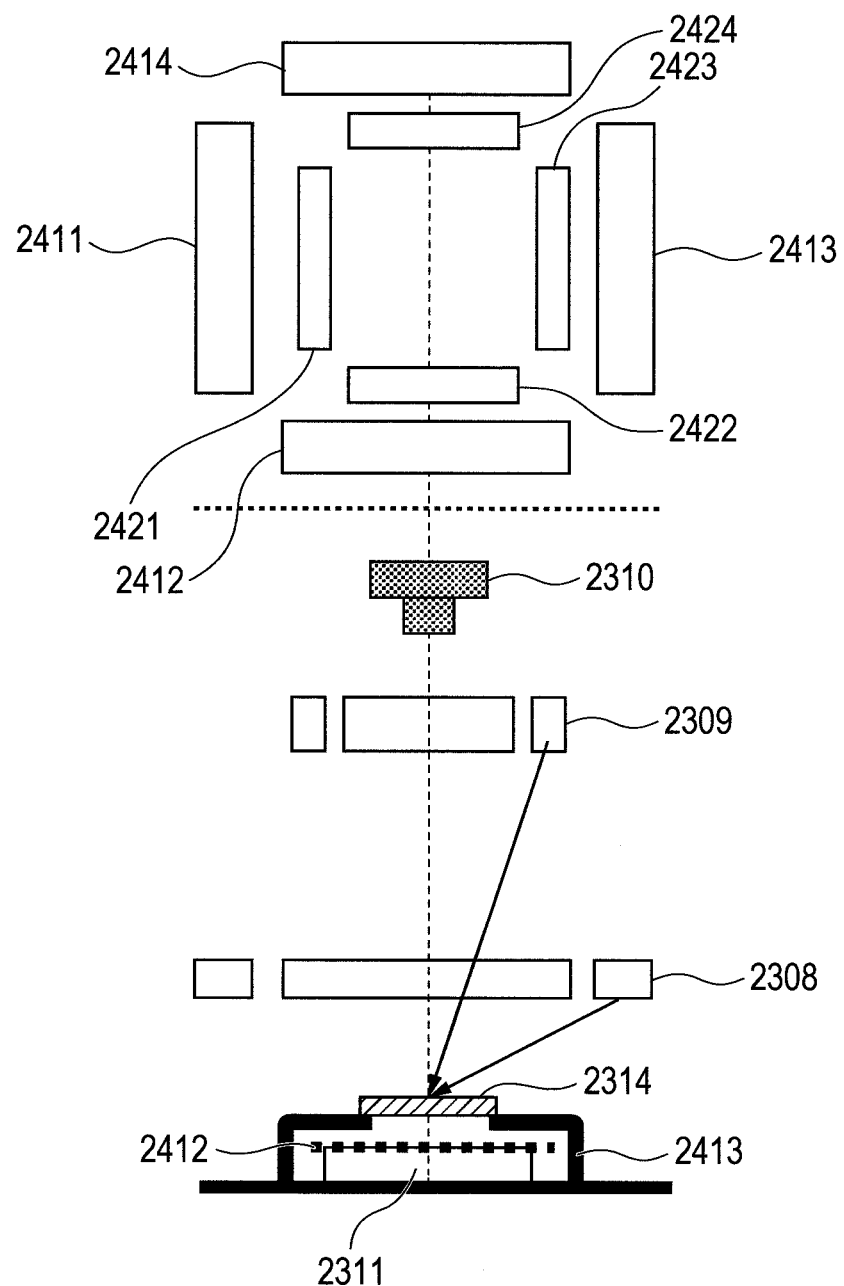
FIG. 24 is an embodiment of an imaging unit based on the present invention.

An embodiment of illumination placement of the bacterial colony imaging unit 2302 is shown in FIG. 24. Reference numeral 2408 represents a low-angle illumination unit, reference numeral 2409 represents a high-angle illumination unit, reference numeral 2410 represents a camera, and reference numeral 2411 represents a transmitted illumination unit. Reference numeral 2412 represents a light shielding plate, reference numeral 2413 represents a base, and reference numeral 2414 represents a set petri dish. Referring back to FIG. 23, the bacterial colony acquired from the specimen is grown on the surface of the agar medium in the petri dish 2314.

The low-angle illumination unit 2308, the high-angle illumination unit 2309, and the transmitted illumination unit 2311 are connected to an illumination control unit 2315 and may illuminate the petri dish through a predetermined combination. When the transmitted illumination unit 2311 is lit on, illumination light is set to illuminate the petri dish 2314, and further, when the low-angle illumination unit 2308 and the high-angle illumination unit 2309 are lit on, a bottom surface of the petri dish 2314 is darkened. The bacterial colony on the petri dish 2314 is imaged by the camera 2310 and the acquired image is transmitted to the image input means 2316. Reference numeral 2317 represents an image processing means, which extracts an area of the bacterial colony by processing image data transmitted to the image input means 2316, and further, an image feature amount from each extracted bacterial colony is calculated by using the image processing means 2317. The image feature amount includes, for example, a boundary length, an area, color information, luminosity information, and a difference from background luminosity of the bacterial colony area. Reference numeral 2318 represents a secondary storage device and may store the imaged image, the processed image, data, and the position and the area of the bacterial colony. The image processing means 2317 analyzes the acquired feature amount and performs grouping of a plurality of kinds of bacterial colonies on the petri dish based on a past database received in the secondary storage device 2318.

The petri dish after imaging is transported to the bacterial colony harvesting unit 2304 by a transportation means 2319. Reference numeral 2320 represents a harvesting needle, reference numeral 2321 represents a Z stage, and reference numeral 2322 represents an XY stage. Inputted image information is projected on a monitor 2323 and a laboratory technician selects and determines a plurality of bacterial colonies to be harvested. Determination information is transferred to the bacterial colony harvesting unit 2304 together with the position of the bacterial colony. By controlling the Z stage 2321 and the XY stage 2322, the harvesting needle 2320 is moved to the coordinate of the bacteria colony of the petri dish 2314 to pick up the bacterial colony.

FIG. 24 shows a detailed configuration diagram of the imaging unit of FIG. 23. The low-angle illumination unit 2308 is constituted by low-angle illumination units 2411, 2412, 2413, and 2414 and light-on thereof may be individually controlled by using an illumination control unit 2315. The high-angle illumination unit 2309 is constituted by high-angle illumination units 2421, 2422, 2423, and 2424 and light-on thereof may also be individually controlled. Since the surface of the bacterial colony is comparatively smooth, a spot subjected to direct reflection is imaged brightly by adjusting the illumination.

The illumination is lit on for each direction to acquire luminosities in the illumination, at the center of the bacterial colony, and on a surface including the optical axis of the camera. In acquiring a detailed shape of the bacterial colony, it is preferable to combine several kinds of images by imaging among those of four types of images illuminated by the low-angle illumination units 2411, 2412, 2413, and 2414, respectively one by one, four types of images illuminated by the high-angle illumination units 2421, 2422, 2423, and 2424, respectively one by one, the image illuminated by the transmitted illumination unit 2311 and images which are imaged by the illumination from plural directions simultaneously.

In the high-angle illumination, according to the position of reflection light, an angle of the bacterial colony at the position of the reflection light may be acquired. The normal-line direction of the bacterial colony at the position of the bacterial colony acquiring the directly reflected light is expressed by (Vc+Vi)/2 by using a unit vector Vc from the position of the reflection light toward the camera lens and a unit vector Vi from the position of the reflection light to the illumination. When the bacterial colony is flat, a position where the reflected light is detected may be estimated to be around the center of the bacterial colony and when the position of the reflected light is around the bacterial colony, the bacterial colony may be estimated to have a height from the culture medium. Further, when the bacterial colony has a shape collapsed from a dome shape, the reflected light from it is detected at a plurality of positions. After the bacterial colony is extracted, the image feature amount is calculated for each bacterial colony. Feature amounts such as the size, color, surface irregularity, shape, or the like of the area of the detected bacterial colony are extracted by image processing using the high-angle illumination image (illuminated by 2309), the low-angle illumination image (illuminated by 2308), and the transmitted illumination image (illuminated by 2311). Further, the circularity is acquired by using the long axis/short axis when the shape is elliptically approximated. The luminosity, color, transmittance, and cubic shape of the bacterial colony are acquired from the transmitted illumination image. The transmittance and the height from the culture medium may be acquired based on the luminosity and direct reflection of the high-angle illumination image.

The transmitted illumination may be used only when the culture medium transmits light, and in this case, the transmitted illumination becomes dark at the position of the bacterial colony, and the thickness of the bacterial colony increases, and further, becomes dark. When any luminosity in the bacterial colony is set as IC(x, y) and an average value of the luminosity of the medium is set as IM, the thickness D(x, y) of the colony at a position of (x, y) is acquired by an equation (Eq. 7) below.

$$D(x,y) = -G(\log IC(x,y) - \log IM) \quad \text{(Eq. 7)}$$

Herein, G represents a gain determined for each bacterial colony species.

It is assumed that the reflected light by the high-angle illumination can be detected at a position (X, Y). In this case, it is assumed that the normal vector is inclined from the vertical direction by θ. In this case, a change in thickness when the position is deviated by Δx becomes −Δx tan θ. Herein, when a difference of D(x, y) is calculated, an equation below is established.

$$D(X+\Delta x, Y) - D(X, Y) = -G(\log IC(X+\Delta x, Y) - \log IC(X, Y)) = -\Delta x \tan\theta \quad (Eq.\ 8)$$

$$G = \Delta x \tan\theta / (\log IC(X+\Delta x, Y) - \log IC(X, Y)) \quad (Eq.\ 9)$$

That is, G is acquired by the equation above, and as a result, the thickness of the bacterial colony is acquired at any position. G shown by (Eq. 9) is constant in the same bacterial colony specimen (alternatively, bacterial colony). G is acquired in the place where direct reflection of the high-angle illumination is detected. The G may be used even in a place where direct reflection cannot be detected. The cubic shape is determined by acquiring the height. The height is determined by luminosity and G at (x, y) acquired by the transmitted illumination image. G is determined by information of direct reflection in the high-angle illumination image. Since G is constant in the same bacterial colony species (alternatively, bacterial colony), only one point at any reflected point (x, y) is sufficient.

Accordingly, in the case of a medium having comparatively high transmittance, when only a place where directly reflected light is generated is discovered, the cubic shape and volume of the bacterial colony may be acquired. The volume may be acquired by integrating the acquired thickness (height) with an area.

As described above, logically, in order to acquire the volume, the volume may be calculated only by the high-angle illumination and the transmitted illumination and the low-angle illumination is not necessarily required. However, in the high-angle illumination, direct reflection causes the shape of the bacterial colony not to be known in some bacterial colonies (in case the periphery and the edge of the bacterial colony are reflected). In this case, the low-angle illumination may be used instead of the high-angle illumination.

Figure 25:
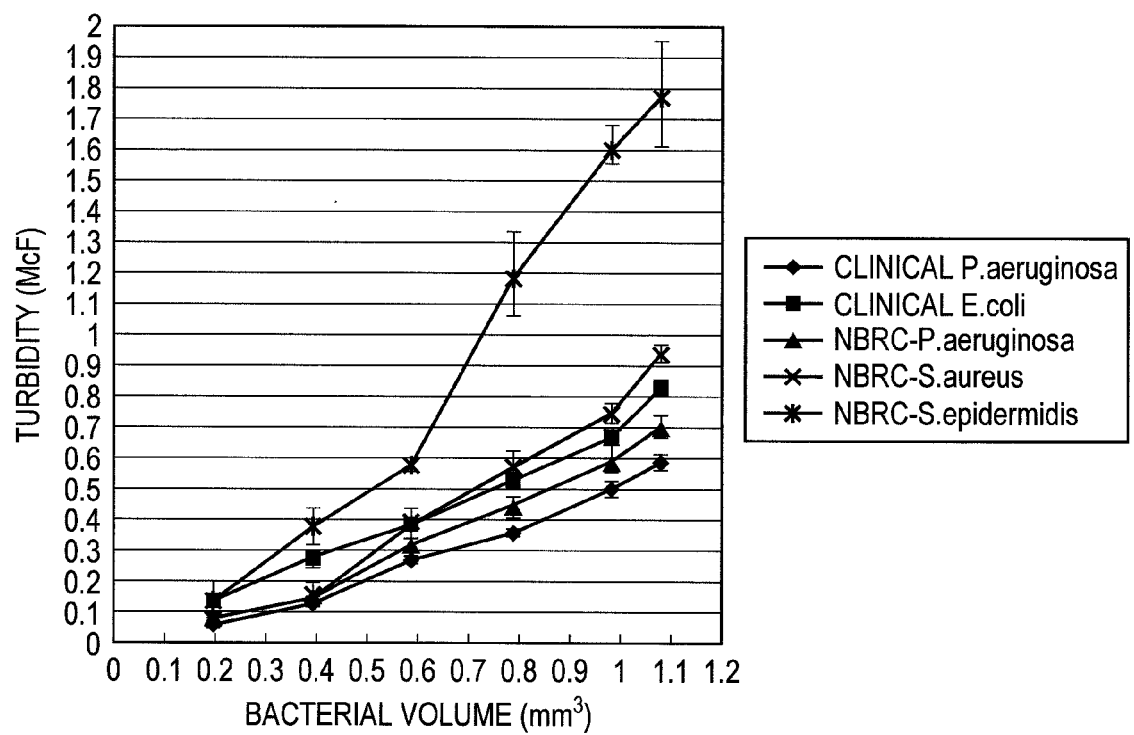
FIG. 25 is a relationship of the volume and the turbidity of the bacterial colony.

FIG. 25 shows a relationship between the volume (mm$^3$) of the bacterial colony for each bacterial species and turbidity (McF). It can be seen that turbidity of suspended bacterial liquid is different even in the same volume for each bacterial species. It is considered as one of the reasons that this difference is caused due to a difference of a content of polysaccharide such as mucoid configuring a cell wall for each bacterium. According to FIG. 25, in the case where 3 Ml of a bacterial liquid having McF of 0.6 is prepared, when at least the bacterial colony of 1 mm$^3$ or more is collected from a total amount, the bacterial liquid is prepared with higher concentration than McF of 0.6 in almost bacterial species. When 1 mm$^3$ is divided by the calculated volume of the bacterial colony according to the method of the present invention, the minimum number of bacterial colonies required to prepare the bacterial liquid may be acquired. Meanwhile, since turbidity per predetermined volume is different for each bacterial species as shown in FIG. 25, when the bacterial species of the bacterial colony is known, the number of bacterial colonies required to prepare the bacterial liquid may be calculated more accurately. However, in general, during bacteria testing, the bacterial species is not identified at this time and a name of a bacterial species may not be known in harvesting. Herein, in the present invention, as described above, the image of the bacterial colony is analyzed in illumination in a plurality of directions, the feature amount is extracted, the bacterial colonies are grouped by a database which is stored in advance, and a kind of the bacterial colony is estimated. When grouping is accomplished, turbidity per predetermined volume may be known from the database and the number of harvested bacteria required to prepare the bacterial liquid may be acquired more accurately by considering the estimated volume of the bacterial colony acquired from the image and a coefficient for each bacterial species. For reference, the number of harvested bacteria required to actually acquire predetermined turbidity is shown in FIG. 26.

When grouping is impossible, the number of harvested bacteria may be calculated with a fixation value according to a bacterial species having the lowest turbidity. As described above, the volume of each bacterial colony is acquired by the image processing means 2317, and further, the number of bacterial colonies required to acquire a predetermined concentration of bacterial liquid is calculated. The information is transferred to the bacterial colony harvesting unit 2304. The bacterial colony harvesting unit 2304, according to the positional information of the bacterial colony to be harvested and information on the required number of bacterial colonies, harvests the plurality of bacterial colonies and suspends the harvested bacterial colonies to the normal saline in a test tube 2324. The turbidity of the suspended bacteria liquid is measured by a turbidimeter (not shown), the required amount of diluted solutions is calculated, the normal saline as the diluted solution is added, the turbidity is verified again, and when the turbidity is predetermined turbidity, the test tube is discharged.

Meanwhile, when accurate thickness information of the bacterial colony is not acquired, thickness information prescribed as several degrees (high, medium, and low) according to an area of the bacterial colony is stored in the secondary storage device 2318 in advance and the thickness information may be automatically corresponded according to the area of the bacterial colony acquired by the image processing means 2317 based on the imaged image and an approximate volume may be estimated. The thickness information to be stored may be set for each bacterial species or may have a predetermined value according to a feature of the shape of the bacterial colony by the bacterial species. When grouping succeeds, accurate thickness information unique to the bacterial species is used and the volume of the bacterial colony may be estimated by multiplying the thickness information by the area of the bacterial colony calculated from the imaged image. When grouping is not performed, a predetermined value depending on the area, which does not depend on the bacterial species is extracted from the secondary storage device 3218 and used to acquire the approximate volume. Further, the thickness information is not automatically calculated according to the area, but a user may input information from the image processing unit 2030 or select and designate the information from candidates of several degrees.

Figure 27:
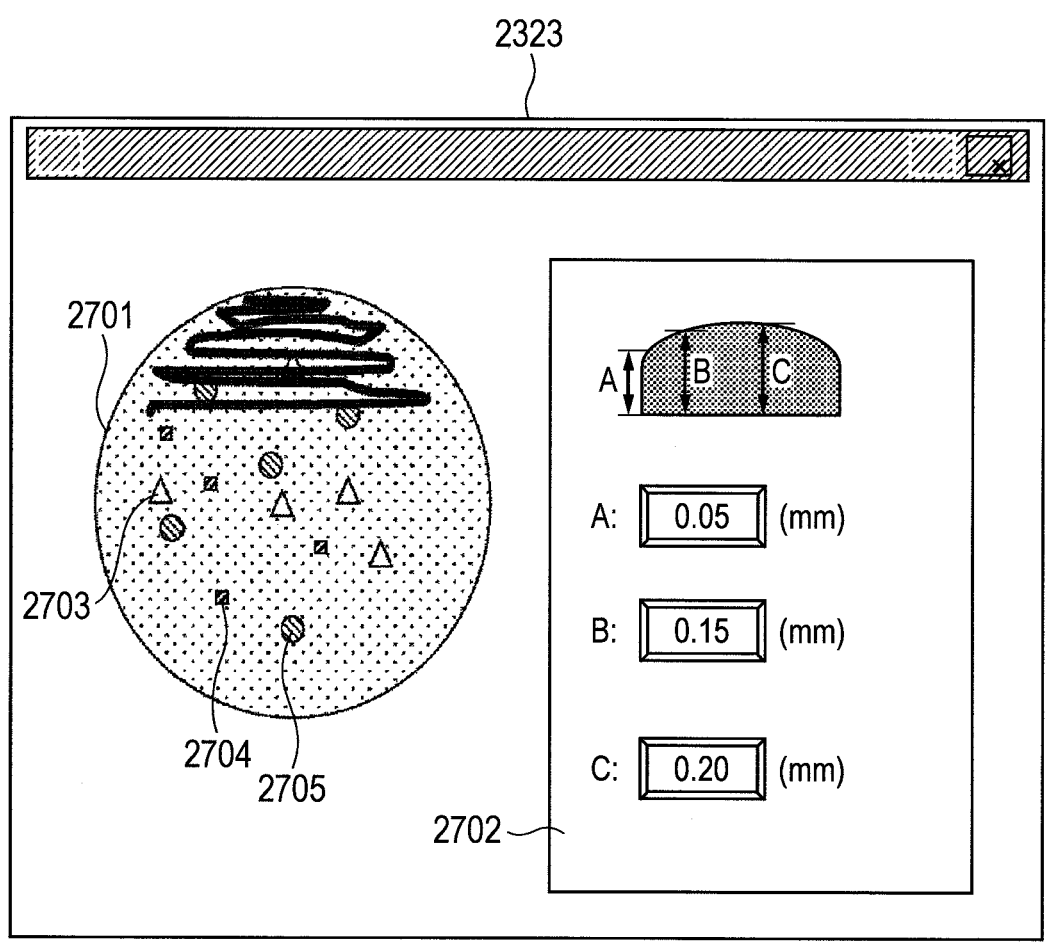
FIG. 27 is a display example of a monitor.

FIG. 27 shows an example of a screen for input. A thickness input area 2702 is present on a monitor 2323 in addition to a bacterial colony image area 2701. The image of the bacterial colony on the petri dish picked up by the camera 2310 is processed, and herein, the bacterial colonies are classified into three groups of 2703 (group α), 2704 (group β), and 2705 (group γ) and are displayed on the bacterial colony image area. The user inputs the thicknesses such as an end thickness (A) of 0.1 mm, a middle portion thickness (B) of 0.15 mm, and a center portion thickness (C) of 0.2 mm with respect to, for example, the bacterial colony of group α of 2703. The input is performed for each group of the bacterial colony to be harvested. Alternatively, the values of A, B, and C may have options, respectively, and may be selected.

Figure 28:
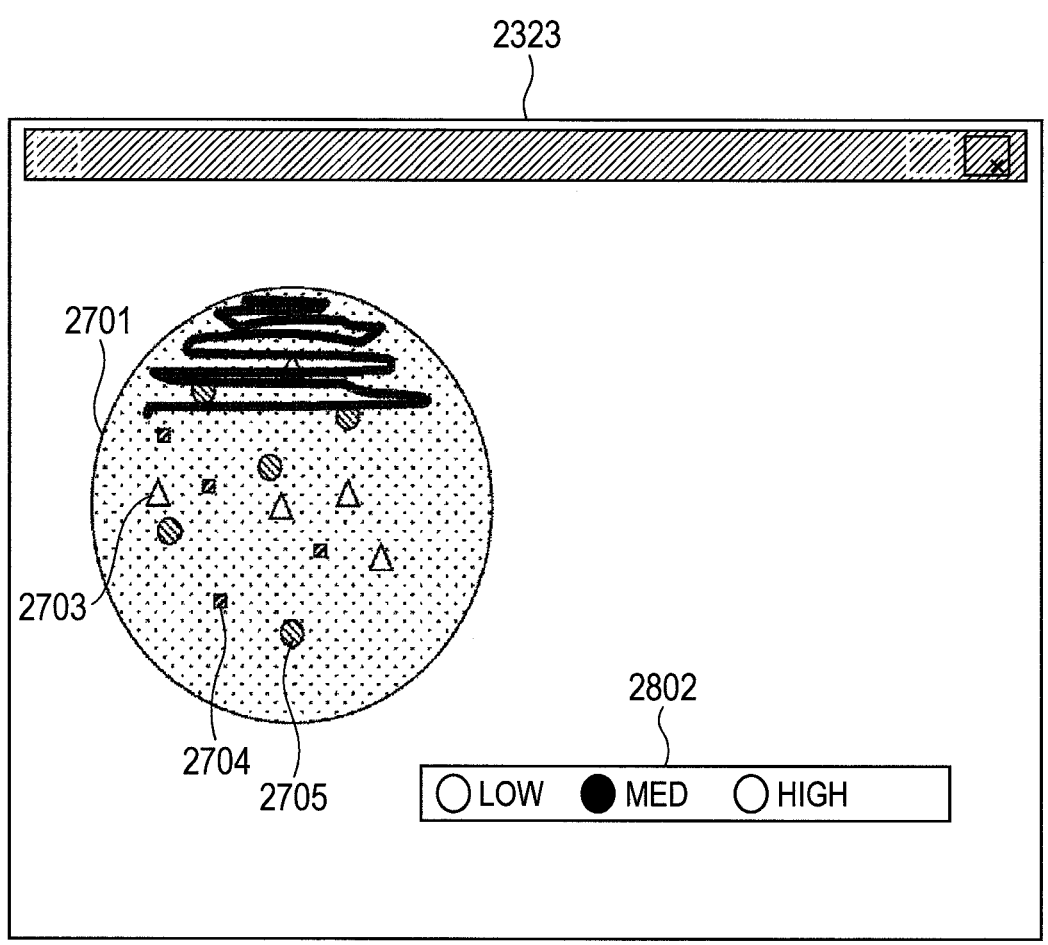
FIG. 28 is another display example of the monitor.

FIG. 28 shows an example of another screen. The thickness of one spot of the bacterial colony may be inputted or selected. The user's input is further simplified and any one of low, medium and high is selected in the thickness input area 2802. Herein, an example of selecting medium is shown. The method for calculating the number of bacterial colonies to be harvested from the relationship between the volume and the turbidity after calculating the volume is the same as the process when the height information is accurately acquired. Further, when a predetermined bacterial species is assumed and thus grouping by the feature amount of the bacterial colony is not required, like a case in which the method is used in an industrial field, a combination of the plurality of illuminations of the low-angle illumination unit 2308, the high-angle illumination unit 2309, and the transmitted illumination unit 2311 is not required, the configuration of the device is simplified, and a manufacturing cost can also be reduced. In this case, the area may be calculated from the imaged image by the image processing means 2317, predetermined thickness information may be input or selected from the plurality of candidates, and the approximate volume may be acquired by multiplying the thickness information by the area.

INDUSTRIAL APPLICABILITY

The present invention can be applied to a device for harvesting a bacterial colony that cultures bacteria in a specimen, selects a bacteria colony, and adjusts a bacterial liquid of the selected bacterial colony in order to identify bacteria included in the specimen and test drug susceptibility.

REFERENCE SIGNS LIST

101 . . . Low-angle illumination unit
102 . . . High-angle illumination unit
103 . . . Camera
104 . . . Transmitted illumination unit
105 . . . Light shielding plate
106 . . . Base
107 . . . Petri dish
108 . . . Petri dish transportation means
109 . . . Stacker
110 . . . Petri dish transportation means
111 . . . Harvesting needle
112 . . . Z stage
113 . . . XY stage
114 . . . Petri dish
115 . . . Light control unit
116 . . . Stage control unit
117 . . . Image input means
118 . . . Grouping means
119 . . . Image processing means
120 . . . Transmitted illumination unit
121 . . . upper illumination unit
122 . . . Camera
123 . . . Micro plate
124 . . . GUI
125 . . . Secondary storage device
130 . . . Input/output means
140 . . . Entire control unit
1800 . . . Petri dish
1801 . . . First buffer station
1802 . . . First transportation means
1803 . . . Imaging stage
1804 . . . Image imaging camera
1805 . . . Second transportation means
1806 . . . Second buffer station
1807 . . . Third transportation means
1808 . . . Harvesting stage
1809 . . . Image display means
1810 . . . Harvesting tool
1811 . . . Rail
1812 . . . Test tube
1813 . . . Bacterial liquid concentration adjusting system
1814 . . . Suspension discharging system
1815 . . . Suspension rack
1820 . . . Control unit
1821 . . . Image outputting device
1901 . . . Non-isolated bacterial colony
1902 . . . Bacterial colony A
1903 . . . Bacterial colony B
2102 . . . Rotational stage
2103 . . . Marker
2104 . . . Photo sensor
2200 . . . Petri dish
2201 . . . First buffer station
2202 . . . First transportation means
2203 . . . Imaging and harvesting stage
2204 . . . Image imaging and displaying camera
2205 . . . Test tube
2206 . . . Bacterial liquid concentration adjusting system
2207 . . . Second transportation means
2208 . . . Second buffer station
2209 . . . Third transportation means
2210 . . . Suspension discharging system
2211 . . . Suspension rack
2220 . . . Control unit
2301 . . . Petri dish supply stacker
2302 . . . Imaging unit (bacterial colony imaging unit)
2303 . . . Image processing unit
2304 . . . Bacterial colony harvesting unit
2305 . . . Bacterial liquid preparing unit
2306 . . . Discharge stacker
2307, 2319 . . . Transportation means
2308 . . . High-angle illumination unit
2309 . . . Low-angle illumination unit
2310 . . . Camera
2311 . . . Transmitted illumination unit
2312 . . . Light shielding plate
2313 . . . Base
2314 . . . Petri dish
2315 . . . Illumination control unit
2316 . . . Image input means
2317 . . . Image processing means
2318 . . . Secondary storage device
2320 . . . Harvesting needle
2321 . . . Z stage
2322 . . . XY stage
2323 . . . Monitor
2324 . . . Test tube
2701 . . . Bacterial colony image area
2702 . . . Thickness input area
303 . . . Group α
304 . . . Group β
305 . . . Group γ
2411, 2412, 2413, 2414 . . . Low-angle illumination unit
2421, 2422, 2423, 2424 . . . High-angle illumination unit

The invention claimed is:

1. A device for harvesting a bacterial colony, comprising:
an upper illumination unit comprising a high-angle illumination unit and a low-angle illumination unit, the high-angle illumination unit and the low angle illumination unit both configured to illuminate a bacterial culture on a culture medium received in a first vessel, which is optically transparent, from above;

a transmitted illumination unit configured to illuminate the bacterial culture by transmitting the optically transparent vessel and the culture medium with illumination light;

an imaging unit configured to sequentially acquire an image the bacterial culture illuminated by high-angle illumination unit of the upper illumination unit, an image of the bacterial culture illuminated by the low-angle illumination of the upper illumination unit, wherein said low-angle illumination image is not produced from directly reflected light and includes color information, and an image of the bacterial culture illuminated by the transmitted illumination unit;

an image processing unit configured to extract an image of a bacterial colony within the bacterial culture to be harvested by processing the image of the bacterial culture illuminated by the high-angle illumination unit of the upper illumination unit, the image of the bacterial culture illuminated by the low-angle illumination unit, and the image of the bacterial culture illuminated by the transmitted illumination unit;

a harvesting unit configured to harvest from the culture medium the bacterial colony corresponding to the image extracted by the image processing unit move the harvested bacterial colony to a second vessel; and a harvested bacteria number calculating unit configured to calculate the number of harvested bacteria required to prepare a bacterial liquid having a predetermined concentration by using thickness information of the bacterial colony of several steps prepared in advance according to the size of an area of the bacterial colony from the image of the bacterial colony extracted with the image processing unit.

2. The device for harvesting a bacterial colony according to claim 1, wherein the thickness information of the bacterial colony is capable of being set by a user.

3. A method for harvesting a bacterial colony, comprising:

illuminating from a high angle and a low angle a bacterial culture on a culture medium received in a first vessel, which is optically transparent, from above and imaging the bacterial culture when illuminated from the high angle to acquire above high angle illumination image of the bacterial culture and imaging the bacterial culture when illuminated from the low angle to acquire an above low angle illumination image of the bacterial culture, wherein said low-angle illumination image is not produced from directly reflected light and includes color information;

illuminating the bacterial colony by transmitting the optically transparent vessel and the culture medium with illumination light from below the first vessel and imaging the bacterial culture to acquire a transmitted light illumination image of the bacterial culture;

extracting an image of a bacterial colony within the bacterial culture to be harvested by processing the high angle illumination image, the low angle illumination image and the transmitted light illumination image; and harvesting the bacterial colony corresponding to the extracted image from the culture medium and moving the harvested bacterial colony to a second vessel, wherein the number of harvested bacteria required to prepare a bacterial liquid having a predetermined concentration is calculated by using thickness information of the bacterial colony of several steps prepared in advance according to the size of an area of the bacterial colony from the image of the bacterial colony of the upper imaged image.

4. The method for harvesting a bacterial colony according to claim 3, wherein the thickness information of the bacterial colony is capable of being set by a user.

* * * * *